(12) United States Patent
Serafin et al.

(10) Patent No.: US 8,765,630 B2
(45) Date of Patent: Jul. 1, 2014

(54) CATALYSTS HAVING ENHANCED STABILITY, EFFICIENCY AND/OR ACTIVITY FOR ALKYLENE OXIDE PRODUCTION

(75) Inventors: Juliana G. Serafin, Charleston, WV (US); Albert C. Liu, Charleston, WV (US); Seyed R. Seyedmonir, Charleston, WV (US); Hwaili Soo, Charleston, WV (US); Thomas Szymanski, Hudson, OH (US)

(73) Assignee: Dow Technology Investments LLC

( * ) Notice: Subject to any disclaimer, the term of this patent is extended or adjusted under 35 U.S.C. 154(b) by 0 days.

(21) Appl. No.: 12/713,020

(22) Filed: Feb. 25, 2010

(65) Prior Publication Data

US 2010/0173771 A1  Jul. 8, 2010

Related U.S. Application Data

(63) Continuation of application No. 10/573,694, filed as application No. PCT/US2004/033219 on Oct. 7, 2004, now abandoned.

(60) Provisional application No. 60/511,975, filed on Oct. 16, 2003.

(51) Int. Cl.
| | |
|---|---|
| B01J 21/00 | (2006.01) |
| B01J 23/58 | (2006.01) |
| B01J 23/56 | (2006.01) |
| B01J 23/02 | (2006.01) |
| B01J 23/04 | (2006.01) |
| B01J 23/00 | (2006.01) |

(52) U.S. Cl.
USPC ........... 502/242; 502/330; 502/332; 502/344; 502/351

(58) Field of Classification Search
USPC .................. 500/232, 236, 239, 242, 300–355
See application file for complete search history.

(56) References Cited

U.S. PATENT DOCUMENTS

| | | | |
|---|---|---|---|
| 2,593,097 A | 4/1952 | Burt et al. | |
| 3,962,136 A | 6/1976 | Nielsen et al. | |
| 4,379,134 A | 4/1983 | Weber et al. | |
| 4,761,394 A | 8/1988 | Lauritzen | |
| 4,829,044 A | 5/1989 | Boxhoorn et al. | |
| 4,908,343 A | 3/1990 | Bhasin | |
| 4,994,589 A | 2/1991 | Notermann | |
| 5,057,481 A | 10/1991 | Bhasin | |
| 5,063,195 A | 11/1991 | Jin et al. | |
| 5,100,859 A | 3/1992 | Gerdes et al. | |
| 5,145,824 A * | 9/1992 | Buffum et al. ................. | 502/216 |
| 5,187,140 A * | 2/1993 | Thorsteinson et al. ....... | 502/348 |
| 5,187,241 A | 2/1993 | Buchwalter et al. | |
| 5,242,551 A | 9/1993 | Frank et al. | |
| 5,384,302 A | 1/1995 | Gerdes et al. | |
| 5,733,842 A | 3/1998 | Gerdes et al. | |
| 5,801,259 A | 9/1998 | Kowaleski | |
| 6,203,773 B1 | 3/2001 | Easley et al. | |
| 7,560,411 B2 | 7/2009 | Yeates et al. | |
| 2006/0047130 A1 | 3/2006 | Yeates et al. | |
| 2010/0298128 A1 | 11/2010 | Serafin et al. | |

FOREIGN PATENT DOCUMENTS

| | | | |
|---|---|---|---|
| CA | 1300586 | | 5/1992 |
| CN | 1217233 | | 5/1999 |
| DE | 19959525 | | 6/2001 |
| DE | 10023717 | | 11/2001 |
| EP | 0003642 | | 7/1984 |
| EP | 0266015 | | 4/1991 |
| EP | 0266015 | | 12/1991 |
| EP | 0496386 | | 1/1992 |
| EP | 0480537 | | 4/1992 |
| EP | 0352850 | | 1/1994 |
| EP | 0393785 | | 1/1995 |
| EP | 0480538 | | 9/1998 |
| EP | 1281706 | | 2/2003 |
| EP | 1308442 | | 5/2003 |
| EP | 1308442 A1 * | 5/2003 |
| EP | 1308442 | | 2/2008 |
| EP | 2277622 | | 1/2011 |
| EP | 1675678 | | 9/2011 |
| WO | 95/01837 | | 1/1995 |
| WO | 00/15333 | | 3/2000 |
| WO | 00/15334 | | 3/2000 |
| WO | 00/15335 | | 3/2000 |
| WO | 03/044003 | | 5/2003 |
| WO | 2005/023417 | | 3/2005 |
| WO | 2005/039757 | | 5/2005 |

OTHER PUBLICATIONS

Kirk-Othmer Encyclopedia of Chemical Technology, 3rd edition, vol. 9, 1980, pp. 445-447, Yeates Ex. 2007.

S. Brunauer, P.H. Emmett & E. Teller, "Adsorption of Gases in Multimolecular Layers" J. of Amer. Chem. Soc., vol. 60 (1938); pp. 309-319, Yeates Ex. 2008.

Serafin, U.S. Appl. No. 12/846,984, filed Jul. 30, 2011, Yeates Ex. 2014.

Serafin, U.S. Appl. No. 12/533,322, filed Jul. 31, 2009, Yeates Ex. 2015.

Serafin, U.S. Appl. No. 10/573,694, filed Jun. 19, 2006, Yeates Ex. 2016.

(Continued)

Primary Examiner — Anthony J Zimmer

(57) ABSTRACT

A catalyst for the manufacture of alkylene oxide, for example ethylene oxide, by the vapor-phase epoxidation of alkene containing impregnated silver and at least one efficiency-enhancing promoter on an inert, refractory solid support, said support incorporating a sufficient amount of zirconium component (present and remaining substantially as zirconium silicate) as to enhance at least one of catalyst activity, efficiency and stability as compared to a similar catalyst which does not contain the zirconium component.

10 Claims, No Drawings

(56) References Cited

OTHER PUBLICATIONS

Serafin, PCT Application PCT/US2004/033218, as filed Oct. 7, 2004, Yeates Ex. 2017.
Serafin, U.S. Appl. No. 60/511,975, filed Oct. 16, 2003, Yeates Ex. 2018.
Response to Written Opinion, filed Aug. 3, 2005, in Serafin PCT Application PCT/US2004/033219, Yeates Ex. 2019.
Response to Written Opinion, filed Dec. 1, 2005, in Serafin PCT Application PCT/US2004/033219, Yeates Ex. 2020.
Supplemental Preliminary Amendment, filed Jan. 12, 2007, in Serafin U.S. Appl. No. 10/573,694, Yeates Ex. 2021.
Second Supplemental Preliminary Amendment, filed Jan. 19, 2007, in Serafin U.S. Appl. No. 10/573,694, Yeates Ex. 2022.
Third Supplemental Preliminary Amendment, filed Feb. 23, 2007, in Serafin U.S. Appl. No. 10/573,694, Yeates Ex. 2023.
Amendment, filed Aug. 8, 2008, in Serafin U.S. Appl. No. 10/573,694, Yeates Ex. 2024.
Response, filed Mar. 2, 2009, in Serafin U.S. Appl. No. 10/573,694, Yeates Ex. 2025.
Amendment and Suggestion for Declaration of Interference Under 37 C.F.R. §41.202, filed Jun. 5, 2009, in Serafin U.S. Appl. No. 10/573,694, Yeates Ex. 2027.
Response to Non-Compliant Amendment, filed Jul. 24, 2009, in Serafin U.S. Appl. No. 10/573,694, Yeates Ex. 2028.
Declaration of Juliana Serafin, signed Apr. 27, 2009, submitted in Serafin U.S. Appl. No. 10/573,694, Yeates Ex. 2068.
Declaration of Albert Liu, signed Apr. 28, 2009, submitted in Serafin U.S. Appl. No. 10/573,694, Yeates Ex. 2069.
Yeates, Provisional U.S. Appl. No. 60/606,193, filed Sep. 1, 2004, Yeates Ex. 2070.
Yeates, U.S. Appl. No. 11/215,267, filed Aug. 30, 2005, Yeates Ex. 2071.
Serafin Suggestion for Declaration of Interference Under 37 C.F.R. §41.202, filed Sep. 9, 2011, in Serafin U.S. Appl. No. 12/846,984, Yeates Ex. 2073.
Horiuchi, et al., Catalysis Letters, 62, 1999, p. 107-111, Yeates Ex. 2074.
Lee et al., Support Participation in Chemistry of Ethylene Oxidation on Silver Catalysts, Applied Catalysis, 44 (1988) 223-237, Yeates Ex. 2075.
Ullmann's Encyclopedia of Industrial Chemistry, 5th, Completely Revised Edition, vol. A 5, p. 351 (1986), Yeates Ex. 2076.
Hawley's Condensed Chemical Dictionary, 13th Ed., p. 40, 41, 44, 45 (1997), Yeates Ex. 2077.
Löcsei (Interceram 1 (1981), p. 38), Yeates Ex. 2078.
Office Action of May 2, 2008, filed in Serafin U.S. Appl. No. 10/573,694, Yeates Ex. 2079.
Submission of Apr. 28, 2009, filed in Serafin U.S. Appl. No. 10/573,694, Yeates Ex. 2080.
Yeates, U.S. Appl. No. 13/470,867, filed May 14, 2012, Yeates Ex. 2081.
Preliminary Amendment filed with Yeates, U.S. Appl. No. 13/470,867, on May 14, 2012 (adding claims 55 and 56), Yeates Ex. 2082.
Yeates Notice of Service of Yeates U.S. Appl. No. 13/470,867, served May 15, 2012, Yeates Ex. 2083.
Transcript of Deposition of Ernest Roger Frank, taken Jun. 13, 2012, in Interference 105,865, Yeates Ex. 2084.
Office Action of Aug. 27, 2009, for Serafin U.S. Appl. No. 10/573,694, Yeates Ex. 2085.
Office Action of Feb. 16, 2011, for Serafin U.S. Appl. No. 12/846,984, Yeates Ex. 2088.
Transcript of Deposition of Dr. Ruth Kowaleski, taken Jun. 6-7, 2012, in Interference 105,865, Yeates Ex. 2089.
Data produced by Dow on Jun. 22, 2012, regarding samples from the 2003 timeframe with XRD and XRF data, Yeates Ex. 2095.
Data produced by Dow on Jun. 22, 2012, regarding sample from the 2011-2012 timeframe with XRD data, Yeates Ex. 2096.
Kirk-Othmer's Encyclopedia of Chemical Technology, 4th Ed. (1994) vol. 9, pp. 915 to 959, Serafin Ex. 1001.
R. Valero, B. Durand, J-L. Guth, T. Chopin, "Hydrothermal Synthesis of Porous Zircon in Basic Fluorinated Medium," Microporous and Mesoporous Materials, vol. 29 (1999) p. 311-318, Serafin Ex. 1003.
"Handbook of Chemistry", N. A. Lange, Editor, McGraw-Hill Book Company, Inc., pp. 1213-1218 (1961), Serafin Ex. 1005.
"CRC Handbook of Chemistry and Physics", 65th Edition, CRC Press, Inc., Boca Raton, Fla., pp. D155-D162 (1984) Ex 1007 J. M. Berty "Reactor for Vapor Phase-Catalytic Studies,", Serafin Ex. 1006.
J. M. Berty "Reactor for Vapor Phase-Catalytic Studies," in Chemical Engineering Progress, vol. 70, No. 5, pp. 78-84, 1974, Serafin Ex. 1007.
Specification of Serafin's U.S. Appl. No. 60/511,975, filed Oct. 16, 2003, Serafin Ex. 1009.
Specification of Serafin's involved U.S. Appl. No. 12/846,984, filed Jul. 30, 2010, Serafin Ex. 1010.
Specification of Serafin's parent U.S. Appl. No. 12/533,322, filed Jul. 31, 2009, Serafin Ex. 1011.
Declaration of Ernest Roger Frank, PhD., dated Apr. 23, 2012, Serafin Ex. 1016.
Supplemental Preliminary Amendment filed on Jan. 12, 2007, in U.S. Appl. No. 10/573,694, Serafin Ex. 1021.
Third Supplemental Preliminary Amendment filed on Feb. 23, 2007, in U.S. Appl. No. 10/573,694, Serafin Ex. 1022.
Suggestion for Interference, filed Sep. 9, 2011, in U.S. Appl. No. 12/846,984, Serafin Ex. 1024.
Declaration under 37 CFR 1.131, filed Aug. 12, 2011, in U.S. Appl. No. 12/846,984, Serafin Ex. 1025.
The Role of Mineralisers in Some Process of Silicate Chemistry, B.P. Locsei, Interceram 1 (1981) 38-42., D5 in Opponent 1.
"The Chemical Behaviour of Zirconium", Warren B. Blumental, D. van Nostrand Co. 1958, p. 214-225, D9 in Opposition 1.
CRC Handbook of Chemistry and Physics, 76th Ed, 1995, p. 4-48), D13 in Opposition 2.
Blumenthal, "The Chemical Behavior of Zirconium", (1958). p. 214-225, D14 in Opposition 2.
Amendment, filed Aug. 12, 2011, in U.S. Appl. No. 12/846,984, Serafin Ex. 1026.
Exhibit A to Declaration under 37 CFR 1.131, filed Aug. 12, 2011, in U.S. Appl. No. 12/846,984, Serafin Ex. 1027.
Exhibit B to Declaration under 37 CFR 1.131, filed Aug. 12, 2011, in U.S. Appl. No. 12/846,984, Serafin Ex. 1028.
Exhibit C to Declaration under 37 CFR 1.131, filed Aug. 12, 2011, in U.S. Appl. No. 12/846,984, Serafin Ex. 1029.
Exhibit D to Declaration under 37 CFR 1.131, filed Aug. 12, 2011, in U.S. Appl. No. 12/846,984, Serafin Ex. 1030.
Exhibit E to Declaration under 37 CFR 1.131, filed Aug. 12, 2011, in U.S. Appl. No. 12/846,984, Serafin Ex. 1031.
Exhibit F to Declaration under 37 CFR 1.131, filed Aug. 12, 2011, in U.S. Appl. No. 12/846,984, Serafin Ex. 1032.
Exhibit G to Declaration under 37 CFR 1.131, filed Aug. 12, 2011, in U.S. Appl. No. 12/846,984, Serafin Ex. 1033.
Exhibit H to Declaration under 37 CFR 1.131, filed Aug. 12, 2011, in U.S. Appl. No. 12/846,984, Serafin Ex. 1034.
Exhibit I to Declaration under 37 CFR 1.131, filed Aug. 12, 2011, in U.S. Appl. No. 12/846,984, Serafin Ex. 1035.
Exhibit J to Declaration under 37 CFR 1.131, filed Aug. 12, 2011, in U.S. Appl. No. 12/846,984, Serafin Ex. 1036.
Exhibit K to Declaration under 37 CFR 1.131, filed Aug. 12, 2011, in U.S. Appl. No. 12/846,984, Serafin Ex. 1037.
Exhibit L to Declaration under 37 CFR 1.131, filed Aug. 12, 2011, in U.S. Appl. No. 12/846,984, Serafin Ex. 1038.
Exhibit M to Declaration under 37 CFR 1.131, filed Aug. 12, 2011, in U.S. Appl. No. 12/846,984, Serafin Ex. 1039.
Second Supplemental Preliminary Amendment filed on Jan. 19, 2007, in U.S. Appl. No. 10/573,694, Serafin Ex. 1041.
Shaklee, C. A. and Messing, G. L. "Growth of $\alpha$-Al2O3 Platelets in the HF-$\gamma$-Al2O3 System," Journal of the American Ceramic Society, (1994) 77: 2977-2984, Serafin Ex. 1046.
Declaration of James A. Wolford, dated Jul. 9, 2012, Serafin Ex. 1047.

(56) References Cited

OTHER PUBLICATIONS

A cover sheet for minutes dated Jan. 2, 2001, from a meeting with individuals from Union Carbide Corporation (UCC) and Saint-Gobain NorPro Corporation held at the UCC Technical Center in S. Charleston, WVA on Dec. 12, 2000, Serafin Ex. 1048.
Declaration of Britt Andrew Vanchura II, PhD., dated Jul. 9, 2012, Serafin Ex. 1050.
Transcription of Oral Deposition of Ruth M. Kowaleski, PhD., taken on Jun. 7, 2012 (vol. 1), Serafin Ex. 1051.
Transcription of Oral Deposition of Ruth M. Kowaleski, PhD., taken on Jun. 8, 2012 (vol. 2), Serafin Ex. 1052.
Electronic Mail from Janelle Waack to Ed Kenehan Sent Friday, Jun. 22, 2012 12:25 PM, with Serafin Production Documents Ex 2090, Ex 2091, Ex 2092, and Ex 2093 Attached, Serafin Ex. 1053.
Transcription of Oral Deposition of Ernest Roger Frank, PhD., taken on Jun. 13, 2012, Serafin Ex. 1055.
Electronic Mail from Ed Kenehan to Janelle Waack Sent Friday, Jun. 22, 2012 1:13 PM, with Serafin Production Documents Bates Stamp Numbered S00001 to S00012 Attached, Serafin Ex. 1056.
Electronic Mail from Ed Kenehan to Janelle Waack Sent Friday, Jun. 22, 2012 1:14 PM, with Serafin Production Documents Bates Stamp Numbered S00013 to S00014 Attached, Serafin Ex. 1058.
Thermal stability of Zircon (ZrSiO4), A. Kaiser et al. Journal of the European Ceramic Society 28 (2008) 2199-2211, D2 in Opposition 1.
Investigation of high-temperature reactions within the ZrSiO4-Al2O3 system, A. Bradecki et al., Ceramics International 36 (2009) 211-214, D4 in Opposition 1.
Email between Kenehan and Waack dated Aug. 23, 2012, serving documents S00113 to S00162.
Email between Kenehan and Petersen dated Aug. 8, 2012, attaching email from Kenehan to Waack of the same date, serving documents S0095 to S00112.
Email between Kenehan and Waack Aug. 1, Jul. 31, 27, Yeates Ex. 2099.
Minutes of Dec. 12 and 13, 2000 Meeting, Yeates Ex. 2101.
Yeates Request for Rehearing served Aug. 24, 2012.
Redacted version of Jan. 2, 2001, Minutes dated Jan. 2, 2001, for the Dec. 20, 2000, meeting of the Dec. 12, 2000 meeting of the UCC-NorPro Project Team in S. Charleston, WVA, Yeates Ex. 2101.
Transcript of Deposition of Britt A. Vanchura, II taken Aug. 7, 2012, in Interference 105,865, Yeates Ex. 2102.
Transcript of Deposition of James A. Wolford, taken Aug. 10, 2012, in Interference 105,865, Yeates Ex. 2103.
"Quantitiative Interpretation of X-ray Diffraction of Patterns of Mixtures. II. Adiabatic Principle of X-ray Diffraction Analysis of Mixtures," J. Appl. Cryst. (1974) vol. 7, pp. 526-530, Yeates Ex. 2115.
Project Report produced by Dow on Aug. 8, 2010, with XRD data, Yeates Ex. 2118.
Third Party Requester's Comments to Patent Owner's Reply of Jun. 13, 2010 Pursuant to 37 C.F.R. §1.947 in Inter Partes Reexamination Control No. 95/001,865, filed Jul. 13, 2012, Serafin Ex. 1063.
Transcription of Oral Deposition of James A. Wolford, taken on Aug. 10, 2012, Serafin Ex. 1066.
Five (5) page version of Exhibit 2057 as served on the party Serafin in connection with the Yeates Motion 2, filed Apr. 24, 2012, Serafin Ex. 1067.
Email sent of Wednesday, Jun. 6, 2012, from Counsel for Yeates to Counsel for Serafin, Serafin Ex. 1068.
Thirty-one (31) page version of Exhibit 2057 as served on the party Serafin on Jun. 6, 2012, Serafin Ex. 1069.
Email sent Wednesday, Jun. 13, 2012, from Counsel for Serafin to Counsel for Yeates, Serafin Ex. 1070.
Amendment, filed Jun. 5, 2009, in Serafin's grandparent U.S. Appl. No. 10/573,694, Serafin Ex. 1071.
Office Action, mailed Oct. 22, 2008, in Yeates' U.S. Appl. No. 11/215, 267, Serafin Ex. 1072.
Paper 116 Yeates Exhibit List as of Aug. 29, 2012.

Serafin Exhibit 1057 in Interference No. 105,865 McK, Serafin Production Documents Bates Stamp No. S00001 to S00012, produced Jun. 22, 2022.
Serafin Exhibit 1059 in Interference No. 105,865 McK, Serafin Production Documents Bates Stamp No. S00013 to S00014, produced Jun. 22, 2012 and referred to in Serafin Opposition 2, Paper No. 68, Jul. 10, 2012.
Serafin Exhibit 1060 in Interference No. 105,865 McK, Graph showing carrier surface area as a function of calcination temperature, based on experiments of Ruth M. Kowaleski, PhD., submitted in connection with Serafin Opposition 2, Paper No. 68, Jul. 10, 2012.
Serafin Exhibit 1061 in Interference No. 105,865 McK, Graph showing crush strength as a function of calcination temperature, based on experiments of Ruth M. Kowaleski, PhD., submitted in connection with Serafin Opposition 2, Paper No. 68, Jul. 10, 2012.
Serafin Exhibit 1068 in Interference No. 105,865 McK, email dated Jun. 6, 2012 from counsel for Yeates to Counsel for Serafin.
Serafin Exhibit 1012 in Interference No. 105,865 McK, Specification of Serafin's grandparent U.S. Appl. No. 10/573,694, filed Mar. 26, 2007.
Yeates Exhibit 2009 in Interference No. 105,865 McK, ASTMD6175-03 (Reapproved 2008, Published Apr. 2008), Standard Test Method for Radial Crush Strength of Extruded Catalyst and Catalyst Carrier Particles.
Yeates Exhibit 2010 in Interference No. 105,865 McK, ASTMD4058-96 (Reapproved 2011, Published Aug. 2011), StandardTest Method for Attrition and Abrasion of Catalysts and Catalyst Carriers.
Yeates Exhibit 2011 in Interference No. 105,865 McK, ASTMC-20-00 (Reapproved 2010, Published May 2010), Standard Test Methods for Apparent Porosity, Water Absorption, Apparent Specific Gravity, and Bulk Density of Burned Refractory Brick and Shapes by Boiling Water.
Yeates Exhibit 2029 in Interference No. 105,865 McK, Declaration of Dr. Ruth Kowaleski, Apr. 23, 2012, submitted in connection with Yeates Motion 2, Paper No. 55, Apr. 24, 2012.
Yeates Exhibit 2030 in Interference No. 105,865 McK CV of Dr. Ruth Kowaleski, submitted in connection with Yeates Motion 2, Paper No. 55, Apr. 24, 2012.
Yeates Exhibit 2031 in Interference No. 105,865 McK, Detailed procedure for synthesis of fluoride mineralized alumina extrudate, submitted in connection with Yeates Motion 2, Paper No. 55, Apr. 24, 2012.
Yeates Exhibit 2032 in Interference No. 105,865 McK, Picture of mixture of components in Lancaster muller, submitted in connection with Yeates Motion 2, Paper No. 55, Apr. 24, 2012.
Yeates Exhibit 2033 in Interference No. 105,865 McK, Picture of wet mixture extruded in a Bonnot extruder, submitted in connection with Yeates Motion 2, Paper No. 55, Apr. 24, 2012.
Yeates Exhibit 2034 in Interference No. 105,865 McK, Picture of dried extrudate particles, submitted in connection with Yeates Motion 2, Paper No. 55, Apr. 24, 2012.
Yeates Exhibit 2035 in Interference No. 105,865 McK, Picture of small, medium, and large crucibles submitted in connection with Yeates Motion 2, Paper No. 55, Apr. 24, 2012.
Yeates Exhibit 2036 in Interference No. 105,865 McK, Picture of arrangement of small, medium and large crucibles during calcinations, submitted in connection with Yeates Motion 2, Paper No. 55, Apr. 24, 2012.
Yeates Exhibit 2037 in Interference No. 105,865 McK, Picture of crucible arrangement Thermolyne high temperature furnace, submitted in connection with Yeates Motion 2, Paper No. 55, Apr. 24, 2012.
Yeates Exhibit 2038 in Interference No. 105,865 McK, Picture of extrudates calcined at 1000C, 1100C, 1200C, 1300C and 1400C, submitted in connection with Yeates Motion 2, Paper No. 55, Apr. 24, 2012.
Yeates Exhibit 2039 in Interference No. 105,865 McK, Picture of extrudate particles prepared for Sem testing in a sample holder with carbon coating, submitted in connection with Yeates Motion 2, Paper No. 55, Apr. 24, 2012.
Yeates Exhibit 2040 in Interference No. 105,865 McK, Picture of Zeiss Supra 40 VP for conducting Sem tests, submitted in connection with Yeates Motion 2, Paper No. 55, Apr. 24, 2012.

(56) References Cited

OTHER PUBLICATIONS

Yeates Exhibit 2041 in Interference No. 105,865 McK, SEM images for extrudate calcined at 1000C for 5 areas magnified 2000X and 10,000X submitted in connection with Yeates Motion 2, Paper No. 55, Apr. 24, 2012.
Yeates Exhibit 2042 in Interference No. 105,865 McK, SEM images for extrudate calcined at 1100C for 5 areas magnified 2000X and 10,000X, submitted in connection with Yeates Motion 2, Paper No. 55, Apr. 24, 2012.
Yeates Exhibit 2043 in Interference No. 105,865 McK, SEM images for extrudate calcined at 1200C for 5 areas magnified 2000X and 10,000X, submitted in connection with Yeates Motion 2, Paper No. 55, Apr. 24, 2012.
Yeates Exhibit 2044 in Interference No. 105,865 McK, SEM images for extrudate calcined at 1300C for 5 areas magnified 2000X and 10,000X, submitted in connection with Yeates Motion 2, Paper No. 55, Apr. 24, 2012.
Yeates Exhibit 2045 in Interference No. 105,865 McK, SEM images for extrudate calcined at 1400C for 5 areas magnified 2000X and 10,000X, submitted in connection with Yeates Motion 2, Paper No. 55, Apr. 24, 2012.
Yeates Exhibit 2046 in Interference No. 105,865 McK, Picture of Micrometrics ASAP 2420 Surface Area testing, submitted in connection with Yeates Motion 2, Paper No. 55, Apr. 24, 2012.
Yeates Exhibit 2047 in Interference No. 105,865 McK, Operating procedures for Micrometrics ASAP 2420 Surface Area Procedure, submitted in connection with Yeates Motion 2, Paper No. 55, Apr. 24, 2012.
Yeates Exhibit 2048 in Interference No. 105,865 McK, Picture of uncrushed dried extrudates loaded into sample cells, submitted in connection with Yeates Motion 2, Paper No. 55, Apr. 24, 2012.
Yeates Exhibit 2049 in Interference No. 105,865 McK, Summary of Loadings and Surface Area Analysis, submitted in connection with Yeates Motion 2, Paper No. 55, Apr. 24, 2012.
Yeates Exhibit 2050 in Interference No. 105,865 McK, Graph of surface area v.s calcination temperature, submitted in connection with Yeates Motion 2, Paper No. 55, Apr. 24, 2012.
Yeates Exhibit 2051 in Interference No. 105,865 McK, Procedure for operating the Micromeritics Autopore IV for measuring porosity, submitted in connection with Yeates Motion 2, Paper No. 55, Apr. 24, 2012.
Yeates Exhibit 2052 in Interference No. 105,865 McK, Picture of Micromeritics Autopore IV, submitted in connection with Yeates Motion 2, Paper No. 55, Apr. 24, 2012.
Yeates Exhibit 2053 in Interference No. 105,865 McK, Porosity measurements and graphs of intrusion vol. versus pore size, submitted in connection with Yeates Motion 2, Paper No. 55, Apr. 24, 2012.
Yeates Exhibit 2054 in Interference No. 105,865 McK, Procedures for determining flat plate crush strength, submitted in connection with Yeates Motion 2, Paper No. 55, Apr. 24, 2012.
Yeates Exhibit 2055 in Interference No. 105,865 McK, Procedure for determination of average particle length and diameter, Corporate Analytical procedure, Rev. 4 submitted in connection with Yeates Motion 2, Paper No. 55, Apr. 24, 2012.
Yeates Exhibit 2056 in Interference No. 105,865 McK, Picture of Dillon TC2 Quantrol i-series instrument for determining crush strength, submitted in connection with Yeates Motion 2, Paper No. 55, Apr. 24, 2012.
Yeates Exhibit 2057 in Interference No. 105,865 McK, Data for particle dimensions and crush strength measurements, submitted in connection with Yeates Motion 2, Paper No. 55, Apr. 24, 2012.
Yeates Exhibit 2058 in Interference No. 105,865 McK, Graph of crush strength vs. calcination temperature, submitted in connection with Yeates Motion 2, Paper No. 55, Apr. 24, 2012.
Yeates Exhibit 2059 in Interference No. 105,865 McK, Summary chart of carrier physical properties, submitted in connection with Yeates Motion 2, Paper No. 55, Apr. 24, 2012.
Yeates Exhibit 2060 in Interference No. 105,865 McK, Sample of ground extrudate in sample holder, submitted in connection with Yeates Motion 2, Paper No. 55, Apr. 24, 2012.

Yeates Exhibit 2061 in Interference No. 105,865 McK, Picture of PanAlytical X'PertPro DY2700 with PIXcel multidetector, submitted in connection with Yeates Motion 2, Paper No. 55, Apr. 24, 2012.
Yeates Exhibit 2062 in Interference No. 105,865 McK, XRD spectrum of the extrudate before calcination, submitted in connection with Yeates Motion 2, Paper No. 55, Apr. 24, 2012.
Yeates Exhibit 2063 in Interference No. 105,865 McK, XRD spectrum of the extrudate after calcination at 1000C, submitted in connection with Yeates Motion 2, Paper No. 55, Apr. 24, 2012.
Yeates Exhibit 2064 in Interference No. 105,865 McK, XRD spectrum of the extrudate after calcination at 1100C, submitted in connection with Yeates Motion 2, Paper No. 55, Apr. 24, 2012.
Yeates Exhibit 2065 in Interference No. 105,865 McK, XRD spectrum of the extrudate after calcination at 1200C, submitted in connection with Yeates Motion 2, Paper No. 55, Apr. 24, 2012.
Yeates Exhibit 2066 in Interference No. 105,865 McK, XRD spectrum of the extrudate after calcination at 1300C, submitted in connection with Yeates Motion 2, Paper No. 55, Apr. 24, 2012.
Yeates Exhibit 2067 in Interference No. 105,865 McK, XRD spectrum of the extrudate after calcination at 1400C, submitted in connection with Yeates Motion 2, Paper No. 55, Apr. 24, 2012.
Yeates Exhibit 2087 in Interference No. 105,865 McK, Ullman's Encyclopedia of Industrial Chemistry, vol. A23, p. 674 (1993).
Yeates Exhibit 2090 in Interference No. 105,865 McK, Laboratory notebook pp. For Kowaleski experiments, Mar. 1, 2012-Mar. 15, 2012.
Yeates Exhibit 2091 in Interference No. 105,865 McK, SEM images for extrudate without added ZrSiO4 calcined at 1000C for 5 areas magnified 2000X and 10,000X, Mar. 8, 2012, submitted in connection with Yeates Opposition 4, Paper No. 74, Jul. 10, 2012.
Yeates Exhibit 2092 in Interference No. 105,865 McK, SEM images for extrudate without added ZrSiO4 calcined at 1400C for 5 areas magnified 2000X and 10,000X, Mar. 7, 2012, submitted in connection with Yeates Opposition 4, Paper No. 74, Jul. 10, 2012.
Yeates Exhibit 2093 in Interference No. 105,865 McK, Data for particle dimensions and crush strength measurements for carriers without added ZrSiO4 Mar. 12, 2012, submitted in connection with Yeates Opposition 4, Paper No. 74, Jul. 10, 2012.
Yeates Exhibit 2094 in Interference No. 105,865 McK, Second declaration of Dr. Ruth Kowaleski, Jul. 10, 2012, submitted in connection with Yeates Opposition 4, Paper No. 74, Jul. 10, 2012.
Yeates Exhibit 2097 referred to as exhibit 2095 in exhibit 2094 in Interference No. 105,865 McK, Graph comparing crush strength of samples with and without added ZrSiO4, Jul. 12, 2012.
Yeates Exhibit 2098 in Interference No. 105,865 McK, Yeates Notice of Cross-Examination and Notice of Intent to Video Record Cross-examination of James A. Wolford, Aug. 2, 2012.
Yeates Exhibit 2111 in Interference No. 105,865 McK, Email communications between Ms. Waack and Mr. Kenehan dated Aug. 15-16, 2012.
Yeates Exhibit 2113 in Interference No. 105,865 McK, Declaration of Dr. David Denley, Aug. 29, 2012.
Yeates Exhibit 2114 in Interference No. 105,865 McK, CV of Dr. David Denley, referred to in Yeates Exhibit 2113, Aug. 29, 2012.
Yeates Exhibit 2116 in Interference No. 105,865 McK, International Center for Diffraction Data Record 01-070-7133, Aug. 29, 2012.
Yeates Exhibit 2117 in Interference No. 105,865 McK, International Center for Diffraction Data Record 00-037-1484, Aug. 29, 2012.
Redacted Invention Disclosure Form currently identified as Unified Reference D1, submitted by Opponent 1 in Opposition to EP167678, in Notice of Opposition and supporting documents filed Jun. 26, 2012.
Experimental Report currently identified as Unified Reference D6, submitted as D6 by Opponent 1 in Opposition to EP167678, in Notice of Opposition and supporting documents filed Jun. 26, 2012.
U.S. Appl. No. 60/511,975 dated Oct. 16, 2003, currently identified as Unified Reference D16, submitted as D16 by Opponent 1 and D10 by Opponent 2 in Opposition to EP167678, in Notice of Opposition and supporting documents filed Jun. 26, 2012 and Jun. 28, 2012, respectively.

(56) References Cited

OTHER PUBLICATIONS

Submission of the Patentee dated Aug. 3, 2005, currently identified as Unified Reference D20, submitted as D11 by Opponent 2 in Opposition to EP167678, in Notice of Opposition and supporting documents filed Jun. 28, 2012.
Submission of the Patentee dated Dec. 1, 2005, currently identified as Unified Reference D21, submitted as D12 by Opponent 2 in Opposition to EP167678, in Notice of Opposition and supporting documents filed Jun. 28, 2012.
WO/ISA of Opposed Patent EP 167678 dated Jan. 13, 2005, currently identified as Unified Reference D23, submitted as D15 by Opponent 2 in Opposition to EP167678, in Notice of Opposition and supporting documents filed Jun. 28, 2012.
Notice of Opposition to EP1676778 by Opponent 1 (Shell International Research Maatschappij BV), Jun. 26, 2012.
Notice of Opposition to EP1676778 by Opponent 2 (Dr. Andrea Hrovat), Jun. 28, 2012.
Dow Response to Notices of Opposition to EP 1676778, Apr. 12, 2013, including Letter to EPO, 1st-4th Auxiliary Requests, Main Request, List of References and Manuscript amended Main Request and 1st-4th Auxiliary Requests.
"Exhibit M"—Redacted project report currently identified as Unified Reference D3, submitted by Opponent 1 in Opposition to EP167678, in Notice of Opposition and supporting documents filed Jun. 16, 2012.
Redacted Dow Chemical report titled "Zircon Modified LAP a Carrier HEC-20 EO catalyst",dated Jul. 14, 2000 currently identified as Unified Reference D30, submitted by Dow in response to Opposition to EP167678.
Analytical Report of the Dow Chemical Company dated Aug. 29, 2003, currently identified as Unified Reference D31, submitted by Dow in response to Opposition to EP167678.
Declaration of James A. Wolford dated Jul. 9, 2012, currently identified as Unified Reference D32, submitted by Dow in response to Opposition to EP167678.
Declaration of Dr. Juliana G. Serafin dated Apr. 27, 2009, currently identified as Unified Reference D33, submitted by Dow in response to Opposition to EP167678.
Serafin Notice Under 37 CFR Section 41.110(b), Paper No. 14 in Interference No. 105,865 McK, Jan. 31, 2012.
Yeates Exhibit 2103 in Interference No. 105,865 McK, Sep. 11, 2012.
Redacted letter from counsel explaining the rejection of the Examiner and enclosing a translation of the Taiwanese search report, May 13, 2013.
Acknowledgement of Settlement Agreement in Interference No. 105,865 McK, Paper No. 348, Mar. 2, 2013.
Notice of Submission in Interference No. 105,865 McK, Paper No. 347, Feb. 19, 2013.
Judgement in Interference No. 105,865 McK, Paper No. 346, Dec. 20, 2012.
Memorandum Opinion and Order in Interference No. 105,865 McK, Paper No. 345, Dec. 20, 2012.
Memorandum Opinion and Order in Interference No. 105,865 McK, Paper No. 344, Dec. 20, 2012.
Yeates Identification of Nature of Additional Discovery in Interference No. 105,865 McK, Paper No. 343, Dec. 11, 2012.
Memorandum Opinion and Order in Interference No. 105,865 McK, Paper No. 342.001, Dec. 11, 2012.
Serafin Response to Paper 337 in Interference No. 105,865 McK, Paper No. 342, Dec. 11, 2012.
Transcript of Oral Hearing Held Nov. 14, 2012 in Interference No. 105,865 McK, Paper No. 341, Dec. 3, 2012.
Yeates Demonstrative Exhibits in Interference No. 105,865 McK, Paper No. 340, entered Nov. 29, 2012.
Serafin Demonstrative Exhibits in Interference No. 105,865 McK, Paper No. 339, entered Nov. 29, 2012.
Second Redeclaration in Interference No. 105,865 McK, Paper No. 338, Nov. 28, 2012.
Order-Conference Call in Interference No. 105,865 McK, Paper No. 337.001, Nov. 28, 2012.
Interlocutory Decision in Interference No. 105,865 McK, Paper No. 336, Nov. 28, 2012.
Serafin Response to Paper No. 334 in Interference No. 105,865 McK, Paper No. 335, Nov. 27, 2012.
Order-Communication in Interference No. 105,865 McK, Paper No. 334, Nov. 15, 2012.
Appearance Record in Interference No. 105,865 McK, Paper No. 333, Nov. 15, 2012.
Yeates Response to Board Invitation to Comment in Interference No. 105,865 McK, Paper No. 332, Nov. 13, 2012.
Serafin Response to Order-Schedule for Oral Argument in Interference No. 105,865 McK, Paper No. 331, Nov. 13, 2012.
Order-Communication in Interference No. 105,865 McK, Paper No. 330, Nov. 9, 2012.
Yeates Demonstratives for Oral Hearing in Interference No. 105,865 McK, Paper No. 329, Nov. 7, 2012.
Serafin Demonstrative Exhibits in Interference No. 105,865 McK, Paper No. 328, Nov. 6, 2012.
Order Schedule for Oral Agument in Interference No. 105,865 McK, Paper No. 327, Nov. 5, 2012.
Serafin Reponse to Yeates Request for Rehearing in Interference No. 105,865 McK, Paper No. 326, Oct. 29, 2012.
Order Granting Serafin Motion 1 in Interference No. 105,865 McK, Paper No. 325, Oct. 23, 2012.
Order Inviting Response to Request for Rehearing in Interference No. 105,865 McK, Paper No. 324, Oct. 12, 2012.
Serafin Submission of the Record in Interference No. 105,865 McK, Paper No. 182, Oct. 10, 2012.
Index of Serafin's Exhibits for the Record in Interference No. 105,865 McK, Paper No. 181, Oct. 10, 2012.
Yeates Notice of Filing of the Record in Interference No. 105,865 McK, Paper No. 136, Oct. 10, 2012.
Yeates Reply 9 in Interference No. 105,865 McK, Paper No. 135, Oct. 13, 2012.
Serafin Reply 11 in Interference No. 105,865 McK, Paper No. 134, Oct. 3, 2012.
Serafin Sur Reply 2 in Interference No. 105,865 McK, Paper No. 133, Oct. 3, 2012.
Yeates Opposition 11 in Interference No. 105,865 McK, Paper No. 132, Sep. 20, 2012.
Serafin Opposition 9 in Interference No. 105,865 McK, Paper No. 131, Sep. 20, 2012.
Order Setting Oral Argument Date in Interference No. 105,865 McK, Paper No. 130, Sep. 12, 2012.
Yeates Request for Oral Hearing in Interference No. 105,865 McK, Paper No. 129, Sep. 11, 2012.
Yeates Exhibit List in Interference No. 105,865 McK, Paper No. 128, Sep. 11, 2012.
Yeates Miscellaneous Motion 9 in Interference No. 105,865 McK, Paper No. 127, Sep. 11, 2012.
Serafin Request for Oral Argument in Interference No. 105,865 McK, Paper No. 125, Sep. 11, 2012.
Serafin Miscellaneous Motion 11 in Interference No. 105,865 McK, Paper No. 124, Sep. 11, 2012.
Serafin Reply 5 in Interference No. 105,865 McK, Paper No. 122, Aug. 29, 2012.
Serafin Reply 4 in Interference No. 105,865 McK, Paper No. 121, Aug. 29, 2012.
Serafin Reply 3 in Interference No. 105,865 McK, Paper No. 120, Aug. 29, 2012.
Yeates Reply 8 in Interference No. 105,865 McK, Paper No. 119, Aug. 29, 2012.
Yeates Reply 7 in Interference No. 105,865 McK, Paper No. 118, Aug. 29, 2012.
Yeates Reply 2 in Interference No. 105,865 McK, Paper No. 117, Aug. 29, 2012.
Memorandum Opinion and Order in Interference No. 105,865 McK, Paper No. 104, Aug. 20, 2012.
Yeates Explanation of Discovery (with corrected Exhibit Nos) in Interference No. 105,865 McK, Paper No. 103, Aug. 16, 2012.
Yeates Notice of Filing of Wolford Transcript in Interference No. 105,865 McK, Paper No. 101, Aug. 16, 2012.

(56) References Cited

OTHER PUBLICATIONS

Serafin Identification of Third Party Counsel in Interference No. 105,865 McK, Paper No. 83, Aug. 16, 2012.
Machine translation of CN1217233.
Redacted letter from counsel explaining the rejection of the Examiner and enclosing a translation of the Taiwanese search report.
Post Deposition Conference Call Order in Interference No. 105,865 McK, Paper No. 82, Aug. 13, 2012.
Post Conference Call Order in Interference No. 105,865 McK, Paper No. 81, Aug. 13, 2012.
Yeates Opposition 5 in Interference No. 105,865 McK, Paper No. 75, Jul. 10, 2012.
Yeates Opposition 4 in Interference No. 105,865 McK, Paper No. 74, Jul. 10, 2012.
Yeates Opposition 3 in Interference No. 105,865 McK, Paper No. 73, Jul. 10, 2012.
Yeates Notice of Unfiled Opposition 1 in Interference No. 105,865 McK, Paper No. 72, Jul. 10, 2012.
Serafin Opposition 8 in Interference No. 105,865 McK, Paper No. 70, Jul. 10, 2012.
Serafin Opposition 7 in Interference No. 105,865 McK, Paper No. 69, Jul. 10, 2012.
Serafin Opposition 2 in Interference No. 105,865 McK, Paper No. 68, Jul. 10, 2012.
Joint Stipulation for Extension of Time Periods 3 and 4 in Interference No. 105,865 McK, Paper No. 65, Jun. 22, 2012.
Yeates Supplemental Clean Copy of Claims in Interference No. 105,865 McK, Paper No. 61, May 15, 2012.
Yeates Motion 8 in Interference No. 105,865 McK, Paper No. 60, May 15, 2012.
Serafin Contingent Responsive Motion 5 in Interference No. 105,865 McK, Paper No. 58, May 15, 2012.
Post Conference Call Order Authorizing Responsive Motions in Interference No. 105,865 McK, Paper No. 57, May 10, 2012.
Yeates Motion 7 in Interference No. 105,865 McK, Paper No. 56, Apr. 24, 2012.
Yeates Motion 2 in Interference No. 105,865 McK, Paper No. 55, Apr. 24, 2012.
Serafin Substantive Motion 4 in Interference No. 105,865 McK, Paper No. 53, Apr. 24, 2012.
Serafin Substantive Motion 3 in Interference No. 105,865 McK, Paper No. 52, Apr. 24, 2012.
Serafin Substantive Motion 1 in Interference No. 105,865 McK, Paper No. 51, Apr. 24, 2012.
Joint Stipulation for Extension of Time Periods 104 in Interference No. 105,865 McK, Paper No. 50, Apr. 16, 2012.
Second Supplemental Order-Motions BD.R 104(c) in Interference No. 105,865 McK, Paper No. 49, Apr. 13, 2012.
Joint Stipulation for Extension of Time for Periods 105 in Interference No. 105,865 McK, Paper No. 48, Mar. 27, 2012.
Serafin Submission of Corrected Filing Receipt in Interference No. 105,865 McK, Paper No. 46, Feb. 8, 2012.
First Supplemental Order—Motion Times in Interference No. 105,865 McK, Paper No. 45, Feb. 7, 2012.
Yeates Supplemental Motions List in Interference No. 105,865 McK, Paper No. 44, Feb. 3, 2012.
Yeates Submission of Non-Patent Literature Mentioned in Interference No. 105,865 McK, Paper No. 31, Feb. 3, 2012.
Serafin Submission of Literature in Interference No. 105,865 McK, Paper No. 23, Feb. 3, 2012.
First Redeclaration in Interference No. 105,865 McK, Paper No. 21, Jan. 31, 2012.
Joint Stipulation Regarding Count 1 in Interference No. 105,865 McK, Paper No. 20, Jan. 30, 2012.
Serafin Notice Regarding Filing Receipt in Interference No. 105,865 McK, Paper No. 19, Jan. 26, 2012.
Serafin Real Party in Interest in Interference No. 105,865 McK, Paper No. 18, Jan. 26, 2012.
Order-Motion Times BD.R. 104(c) in Interference No. 105,865 McK, Paper No. 17, Jan. 20, 2012.
Yeates Motions List in Interference No. 105,865 McK, Paper No. 16, Jan. 17, 2012.
Serafin Motions List in Interference No. 105,865 McK, Paper No. 15, Jan. 17, 2012.
Order BD. R. 109(b) Authorizing Copies of Office Records in Interference No. 105,865 McK, Paper No. 13, Dec. 29, 2011.
Yeates Request for File Copies in Interference No. 105,865 McK, Paper No. 12, Dec. 28, 2011.
Yeates Clean Copy of Claims in Interference No. 105,865 McK, Paper No. 11, Dec. 28, 2011.
Yeates Notice of Related Proceedings in Interference No. 105,865 McK, Paper No. 10, Dec. 28, 2011.
Yeates Notice of Real Party in Interest in Interference No. 105,865 McK, Paper No. 9, Dec. 28, 2011.
Yeates Notice of Lead and Backup Counsel in Interference No. 105,865 McK, Paper No. 8, Dec. 28, 2011.
Serafin Request for File Copies in Interference No. 105,865 McK, Paper No. 7, Dec. 20, 2011.
Serafin Notice of Related Proceedings in Interference No. 105,865 McK, Paper No. 6, Dec. 20, 2011.
Serafin Designation of Real Party in Interest in Interference No. 105,865 McK, Paper No. 5, Dec. 20, 2011.
Serafin Clean Copy of Claims in Interference No. 105,865 McK, Paper No. 4, Dec. 20, 2011.
Serafin Identification of Lead and Backup Counsel in Interference No. 105,865 McK, Paper No. 3, Dec. 20, 2011.
Standing Order in Interference No. 105,865 McK, Paper No. 2, entered Dec. 6, 2011.
Declaration in Interference No. 105,865 McK, Paper No. 1, Dec. 6, 2011.
Serafin Exhibit 1004 in Interference No. 105,865 McK, Periodic Table as published by the Chemical Rubber Company, Cleveland, Ohio, in CRC Handbook of Chemistry and Physics, 46th Edition, inside back cover, 1965.
Serafin Exhibit 1049 in Interference No. 105,865 McK, Redacted copy of Attachment 49 to Ex. 1048 showing an x-ray diffraction pattern of a zircon modified LAP a carrier, identified by Sample No. 9908252, Jan. 2, 2001.
Serafin Exhibit 1054 in Interference No. 105,865 McK, Mesh to Microns Conversion Chart, submitted with Serafin Opposition 2, Paper No. 68, Jul. 10, 2012.

* cited by examiner

CATALYSTS HAVING ENHANCED STABILITY, EFFICIENCY AND/OR ACTIVITY FOR ALKYLENE OXIDE PRODUCTION

CROSS-REFERENCE TO RELATED APPLICATION

This application claims the benefit of U.S. Provisional Patent Application Ser. No. 60/511,975, filed Oct. 16, 2003.

FIELD OF INVENTION

This invention relates to catalysts for the epoxidation of alkene, especially ethylene, to the corresponding alkylene oxide, for example, ethylene oxide, which have enhanced stability, efficiency and/or activity by incorporating sufficient amount of a zirconium component substantially as zirconium silicate.

BACKGROUND OF THE INVENTION

The production of alkylene oxide, such as ethylene oxide, by the reaction of oxygen or oxygen-containing gases with ethylene in the presence of a silver-containing catalyst at elevated temperature is an old and well-known art. For example, U.S. Pat. No. 2,040,782, dated May 12, 1936, describes the manufacture of ethylene oxide by the reaction of oxygen with ethylene in the presence of silver catalysts which contain a class of metal-containing promoters. In Reissue U.S. Pat. No. 20,370, dated May 18, 1937, Leforte discloses that the formation of olefin oxides may be effected by causing olefins to combine directly with molecular oxygen in the presence of a silver catalyst. (An excellent discussion on ethylene oxide, including a detailed description of commonly used manufacturing process steps, is found in Kirk-Othmer's Encyclopedia of Chemical Technology, $4^{th}$ Ed. (1994) Volume 9, pages 915 to 959).

The catalyst is the most important element in direct oxidation of ethylene to produce ethylene oxide. There are several well-known basic components of such catalyst: the active catalyst metal (generally silver as described above); a suitable support/carrier (for example alpha-alumina); and catalyst promoters, all of which can play a role in improving catalyst performance. Because of the importance of the catalyst in the production of ethylene oxide, much effort has been expended to improve catalyst's efficiency in producing ethylene oxide.

The use of zirconium and or silicon components as either promoters in the ethylene oxide catalyst or as modifiers to supports (that is carriers) used for such catalysts are also known.

U.S. Pat. No. 5,703,001 describes a rhenium-free silver catalyst promoted with an alkali metal component and a Group IVB component wherein the Group IVB component is added as a compound having a Group IVB cation. Soluble zirconium compounds where the Group IVB component is a cation are preferred.

U.S. Pat. No. 5,145,824 describes a rhenium-promoted ethylene oxide silver catalyst supported on a carrier comprising alpha alumina, an added alkaline earth metal in the form of an oxide, silicon in the form of an oxide, and from zero to about 10 percent (%) added zirconium in the form of the oxide. In U.S. Pat. No. 5,145,824, the term "oxide" is used to refer to simple oxides made up of only one metal as well as complex oxides made up of the indicated metal and one or more of the other metals. The amount of alkaline earth metal used in the carrier is from 0.05 to 4 weight percent (wt. %), measured as the oxide. Similarly, U.S. Pat. No. 5,801,259 describes an ethylene oxide catalyst comprising silver and promoters on a carrier prepared by mixing alpha alumina, alkaline earth metal oxide, silicon oxide, and from zero to about 15% of zirconium in the form of the oxide. The particle sizes of the ceramic components are chosen such that the packing density of the dried carrier precursor is not greater than that of the fired carrier; thereby eliminating the need for organic burnout agents. In '824 and '259 patents, the carrier mixture is formed from a starting mixture containing alpha-alumina, and requires the addition of alkaline earth metal oxide. The addition of the zirconium oxide component is optional.

There are several examples in the prior art of carriers used for ethylene oxide catalysts which contain silicon-containing compounds. U.S. Pat. No. 6,313,325 describes a method for the production of ethylene oxide wherein the carrier of the catalyst is obtained by adding an aluminum compound, a silicon compound and an alkali metal compound to a low-alkali content alpha-alumina powder. After calcination, this mixture is thought to provide a coating layer of alkali metal-containing amorphous silica alumina on the outer surface of the alpha-alumina carrier and the inner surface of the pores thereof. Canadian patent 1,300,586 describes a catalyst using a carrier composed mainly of alpha-alumina, silica, sodium, which has measurable acidity and crystals of $Al_6Si_2O_{13}$ which are detectable by X-ray Diffraction analysis (XRD).

Several terms are commonly used to describe some of the parameters of catalytic systems for epoxidation of alkenes. For instance, "conversion" is defined as the molar percentage of alkene fed to the reactor which undergoes reaction. Of the total amount of alkene which is converted to a different chemical entity in a reaction process, the molar percentage which is converted to the corresponding alkylene epoxide, that is alkylene oxide, is known as the "efficiency" (which is synonymous with the "selectivity") of that process. The product of the percent efficiency times the % conversion (divided by 100% to convert from $\%^2$ to %) is the percentage "yield", that is, the molar percentage of the alkene fed that is converted into the corresponding epoxide.

The "activity" of a catalyst can be quantified in a number of ways, one being the mole percent of alkylene epoxide contained in the outlet stream of the reactor relative to that in the inlet stream (the mole percent of alkylene epoxide in the inlet stream is typically, but not necessarily, zero percent) while the reactor temperature is maintained substantially constant, and another being the temperature required to maintain a given rate of alkylene epoxide production. That is, in many instances, activity is measured over a period of time in terms of the molar percent of alkylene epoxide produced at a specified constant temperature. Alternatively, activity may be measured as a function of the temperature required to sustain production of a specified constant mole percent of alkylene epoxide. The useful life of a reaction system is the length of time that reactants can be passed through the reaction system during which results are obtained which are considered by the operator to be acceptable in light of all relevant factors.

Deactivation, as used herein, refers to a permanent loss of activity and/or efficiency, that is, a decrease in activity and/or efficiency which cannot be recovered. As noted above, production of alkylene epoxide product can be increased by raising the temperature, but the need to operate at a higher temperature to maintain a particular rate of production is representative of activity deactivation. Activity and/or efficiency deactivation tends to proceed more rapidly when higher reactor temperatures are employed. The "stability" of a catalyst is inversely proportional to the rate of deactivation, that is, the rate of decrease of efficiency and/or activity. Lower rates of decline of efficiency and/or activity are generally desirable.

To be considered satisfactory, a catalyst must have acceptable activity and efficiency, and the catalyst must also have sufficient stability, so that it will have a sufficiently long useful life. When the efficiency and/or activity of a catalyst has declined to an unacceptably low level, typically the reactor must be shut down and partially dismantled to remove the catalyst. This results in losses in time, productivity and materials, for example silver catalytic material and alumina carrier. In addition, the catalyst must be replaced and the silver salvaged or, where possible, regenerated. Even when a catalyst is capable of regeneration in situ, generally production must be halted for some period of time. At best, replacement or regeneration of catalyst requires additional losses in production time to treat the catalyst and, at worst, requires replacement of the catalyst with the associated costs. It is therefore highly desirable to find ways to lengthen the useful life of a catalyst.

SUMMARY OF THE INVENTION

One aspect of the present invention is a catalyst for the manufacture of alkylene oxide by the vapor-phase epoxidation of alkene, said catalyst containing impregnated silver and at least one efficiency-enhancing promoter on a refractory solid support, said support incorporating a sufficient amount of zirconium component to enhance at least one of catalyst activity, efficiency and stability as compared to a similar catalyst which does not contain the zirconium component, said zirconium component being present in the support substantially as zirconium silicate.

Another aspect of the present invention is the catalyst described above wherein the refractory solid support is alpha-alumina, particularly having a unique morphology consisting of interlocking platelets.

Yet another aspect of the present invention is the process for the manufacture of alkylene oxide, such as ethylene oxide or propylene oxide, by the vapor-phase epoxidation of alkene using the improved catalyst of this invention.

While the present invention should be understood as being unconstrained by any particular theory, it is believed that the zirconium silicate (commonly referred to as zircon), added as an ingredient with other raw materials used to form the carrier support, survives the rigors of the calcining process without being oxidized or otherwise undergoing a substantial chemical change, and thereby becomes an integral part of the modified carrier, ultimately contributing to the favorable and unexpected characteristics observed in catalysts of the present invention employing such modified carriers.

A key distinguishing feature of the present invention is the use of zirconium silicate with other raw materials to modify the inert, refractory solid support (such as alpha-alumina) used as a carrier in a manner described herein, prior to depositing silver thereon with a well known promoter (and other optional additives) to convert the carrier to a catalyst. Zirconium silicate is employed in such a way and in sufficient amount that its presence in the modified carrier ultimately enhances the activity, efficiency and/or stability of the resultant catalyst of the present invention. Zirconium silicate remains substantially the same chemically throughout various preparation steps (including multiple calcining or roasting steps involving relatively high temperatures noted herein) for making the catalyst of the present invention, from its initial introduction as a part of raw materials for the modified carrier to the finished catalyst.

DETAILED DESCRIPTION OF THE INVENTION

Alkylene oxides made using the catalysts of this invention are characterized by the structural formula

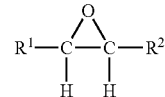

wherein $R^1$ and $R^2$ are lower alkyl, for example, methyl or ethyl or, preferably, hydrogen. Most preferably, the alkylene oxide is ethylene oxide. The alkylene oxides are made from the corresponding alkene, that is, $R^1HC=CHR^2$. The following discussion is presented in terms of and with reference to ethylene oxide and ethylene for the sake of simplicity and illustration. However, the scope and range of the present invention is generally applicable to catalysts for the epoxidation of suitable alkenes.

In commercially useful catalysts for the production of ethylene oxide, the carrier upon which the silver and promoters reside must have a physical form and strength to allow proper flow of gaseous reactants, products and ballast through the reactor while maintaining physical integrity over catalyst life. Significant catalyst breakage or abrasion is highly undesirable because of the pressure drop and safety problems such degradation can cause. The catalyst must also be able to withstand fairly large temperature fluctuations within the reactor. The pore structure and chemical inertness of the carrier are also important factors that must be considered for optimum catalyst performance. Refractory materials, particularly alpha-alumina, have been successfully used as the carrier for ethylene oxide catalysts. Other porous refractory carrier or materials may also be used as long as they are relatively inert in the presence of the reactant feeds introduced for epoxidation and the product epoxide, and are able to withstand preparation conditions when converted into catalyst. For example, carriers may be composed of alpha-alumina, silicon carbide, silicon dioxide, zirconia, magnesia, various clays and mixtures thereof.

The catalyst of the present invention which is useful for the production of an alkylene oxide, such as ethylene oxide, from alkene, such as ethylene, is supported on a zircon-modified carrier. Zircon, a naturally occurring material which is also known as zirconium silicate, has the chemical formula of $ZrSiO_4$. Zircon may also be prepared synthetically, following a number of well-known procedures such as that given in R. Valero, B. Durand, J-L. Guth, T. Chopin, "Hydrothermal Synthesis of Porous Zircon in Basic Fluorinated Medium," Microporous and Mesoporous Materials, Vol. 29 (1999) p. 311-318. In general, the carriers are made up of an inert, refractory support, such as alpha-alumina, having a porous structure and relatively high surface area, which has been modified by the presence of zirconium silicate introduced with the other raw materials used to produce the carrier. In preparing a catalyst of the present invention, silver is deposited throughout the pores of the carrier and reduced to silver metal. Promoters, such as alkali salts, can be added with the soluble silver mixture impregnated into the carrier or added in a separate step. These promoters are generally associated with silver, although they may also be present on the carrier. The promoters act to improve catalyst efficiency, activity and/or stability.

The raw materials for the carrier must be of sufficient purity so that there is limited reaction between any components thereof and the zirconium silicate to be added during the preparation of the carrier in accordance with the teachings of the present invention. Limiting such reaction ensures that the added zirconium silicate remains substantially unchanged chemically throughout the processing of the carrier and the conversion of the carrier into the catalyst. Even the partial decomposition of zirconium silicate to zirconium oxide ($ZrO_2$) is a particularly undesirable reaction, which decreases significantly the benefits from the addition of zirconium silicate to the carrier. At higher zirconium silicate concentrations, the presence of zirconium silicate may be easily ascertained by the use of X-ray diffraction analysis of the fired carrier. At lower zirconium silicate concentrations, zirconium silicate may not be detectable by the same analysis. However, the presence of zirconium and silicon may be detected using elemental analyses, such as X-ray fluorescence. In any case, the beneficial effect on catalyst performance and life are the primary indicator of the presence of zirconium silicate, especially at lower zirconium silicate concentrations.

In addition, the zircon itself must be of sufficient purity so that any impurities therein do not promote decomposition of zircon to zirconia during the preparation of the carrier. Impurities in zircon comprise primarily the inorganic compounds of transition metals (excluding zirconium and halfnium, which naturally occurs with zirconium), and are preferably limited to not more than 1.5 wt. %. More common inorganic compounds of transition metals occurring as impurities in zircon are oxides of transition metals. Two of the common oxide impurities are titania and iron oxides.

In the present invention, the zircon is mixed with the other raw materials for the carrier prior to the final firing at high temperature. The zircon may be incorporated in any number of ways, including the adding of the zircon in the form of powder or flour to the other dry raw materials, followed by mixing and adding of liquid raw materials. The order of addition of the zircon to the other raw materials is not critical.

Suitable shapes for the carrier of this invention include any of the wide variety of shapes known for such catalyst supports, including pills, chunks, tablets, pieces, pellets, rings, spheres, wagon wheels, toroids having star shaped inner and/or outer surfaces, and the like, of a size suitable for employment in fixed bed reactors. Conventional commercial fixed bed ethylene oxide reactors are typically in the form of a plurality of parallel elongated tubes (in a suitable shell) about 1 to 3 inches O.D. and 15-45 feet long filled with catalyst. In such fixed bed reactors, it is desirable to employ carrier formed into a rounded shape, such as, for example, spheres, pellets, rings, tablets and the like, having diameters from about 0.1 inch to about 0.8 inch.

There are many well-known methods of preparing carriers suitable for use in ethylene oxide catalysts. Some of such methods are described in, for example, U.S. Pat. Nos. 4,379,134; 4,806,518; 5,063,195; 5,384,302, U.S. Patent Application 20030162655 and the like. As long as the carrier materials and method of preparation do not substantially decompose zircon, these methods can be employed to prepare the zircon modified carrier of the present invention. For example, an alpha-alumina support of at least 95% purity (exclusive of zirconium component) can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives.

Another method for preparing a carrier of this invention having particularly suitable properties for ethylene oxide catalyst usage comprises mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of modified alpha-alumina carrier.

The modified alpha-alumina carrier prepared by the method described above preferably has a specific surface area of at least about 0.5 $m^2/g$ (more preferably from about 0.7 $m^2/g$ to about 10 $m^2/g$), a pore volume of at least about 0.5 cc/g (more preferably from about 0.5 cc/g to about 2.0 cc/g), purity (exclusive of zirconium component) of at least 99 weight percent alpha-alumina, and median pore diameter from about 1 to about 50 microns. In this case, the modified alpha-alumina carrier comprises particles each of which has at least one substantially flat major surface having a lamellate or platelet morphology which approximates the shape of a hexagonal plate (some particles having two or more flat surfaces), at least 50% of which (by number) have a major dimension of less than about 50 microns.

In the finished carrier of the present invention, including those prepared by the two particular methods described above as a way of illustration, zirconium silicate is present in an amount which is preferably in the range of from about 0.01 to about 10.0% by weight, more preferably from about 0.1 to about 5.0% by weight, and most preferably from about 0.3 to about 3.0% based on the total weight of the finished modified alumina carrier.

While the invention is not constrained by any particular theory, the raw materials used to manufacture the carrier should not contain large amounts of reactive calcium compounds in order to minimize the reaction of these species with the added zirconium silicate, resulting in the formation of less beneficial species, particularly zirconia ($ZrO_2$, also called zirconium oxide). The cumulative concentration of calcium compounds in carrier raw materials should be limited so that the fired carrier (excluding zirconium component) contains less than 2000 ppmw calcium, preferably less than 350 ppmw calcium.

In addition, certain other alkaline earth metal compounds may also promote the decomposition of zirconium silicate to zirconia. The cumulative concentration of alkaline earth metal compounds in carrier raw materials should be limited so that the fired carrier (excluding zirconium component) contains less than 500 ppmw alkaline earth metal (excluding calcium compounds), measured as the alkaline earth metal oxide.

The calcination temperature (firing temperature) of the carrier must also be controlled to limit the thermal decomposition of zircon to zirconia which occurs in the pure state at temperatures above 1540° C.

Catalysts for the production of alkylene oxide, for example ethylene oxide or propylene oxide, may be prepared on the modified supports of the present invention by impregnating the carrier with a solution of one or more silver compounds, as is well known in the art. One or more promoters may be impregnated simultaneously with the silver impregnation, before the silver impregnation and/or after the silver impregnation. In making such a catalyst, the carrier is impregnated (one or more times) with one or more silver compound solutions sufficient to allow the silver to be supported on the carrier in an amount which ranges from about 1 to about 70%, more preferably from about 5 to about 50%, most preferably from about 10 to about 40% of the weight of the catalyst.

Although silver particle size is important, the range is not narrow. Suitable silver particle size can be in the range of from about 100 to 10,000 angstroms.

There are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. A solid promoter is incorporated into the catalyst prior to its use, either as a part of the carrier (that is support) or as a part of the silver component applied thereto. When a solid promoter is added during the preparation of the catalyst, the promoter may be added to the carrier before the silver component is deposited thereon, added simultaneously with the silver component, or added sequentially following the deposition of the silver component on the carrier. Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown.

In contrast, the gaseous promoters are gas-phase compounds and or mixtures thereof which are introduced to a reactor for the production of alkylene oxide (for example ethylene oxide) with vapor-phase reactants, such as ethylene and oxygen. Such promoters, also called modifiers, inhibitors or enhancers, further enhance the performance of a given catalyst, working in conjunction with or in addition to the solid promoters. One or more chlorine-containing components are typically employed as gaseous promoters, as is well known in the art. Other halide-containing components may also be used to produce a similar effect. Depending on the composition of the solid catalyst being employed, one or more gaseous components capable of generating at least one efficiency-enhancing member of a redox half reaction pair may be employed as gaseous promoters, as is well known in the art. The preferred gaseous component capable of generating an efficiency-enhancing member of a redox half reaction pair is preferably a nitrogen-containing component.

The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid promoters will be referred to in terms of cations and anions regardless of their form in the catalyst under reaction conditions.

It is desirable that the silver and optional one or more solid promoters be relatively uniformly dispersed on the zircon-modified carrier. A preferred procedure for depositing silver catalytic material and one or more promoters comprises: (1) impregnating a porous zircon-modified carrier according to the present invention with a solution comprising a solvent or solubilizing agent, silver complex and one or more promoters, and (2) thereafter treating the impregnated carrier to convert the silver salt to silver metal and effect deposition of silver and the promoter(s) onto the exterior and interior pore surfaces of the carrier. Silver and promoter depositions are generally accomplished by heating the carrier at elevated temperatures to evaporate the liquid within the carrier and effect deposition of the silver and promoters onto the interior and exterior carrier surfaces. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

The silver solution used to impregnate the carrier is preferably comprised of a silver compound in a solvent or complexing/solubilizing agent such as the silver solutions disclosed in the art. The particular silver compound employed may be chosen, for example, from among silver complexes, silver nitrate, silver oxide or silver carboxylates, such as silver acetate, oxalate, citrate, phthalate, lactate, propionate, butyrate and higher fatty acid salts. Silver oxide complexed with amines is a preferred form of silver for use in the present invention.

A wide variety of solvents or complexing/solubilizing agents may be employed to solubilize silver to the desired concentration in the impregnating medium. Among those disclosed as being suitable for this purpose are lactic acid; ammonia; alcohols, such as ethylene glycol; and amines and aqueous mixtures of amines.

For example, $Ag_2O$ can be dissolved in a solution of oxalic acid and ethylenediamine to an extent of approximately 30% by weight. Vacuum impregnation of such a solution onto a carrier of approximately 0.7 cc/g porosity typically results in a catalyst containing approximately 25% by weight of silver based on the entire weight of the catalyst. Accordingly, if it is desired to obtain a catalyst having a silver loading of greater than about 25 or 30%, and more, it would generally be necessary to subject the carrier to at least two or more sequential impregnations of silver, with or without promoters, until the desired amount of silver is deposited on the carrier. In some instances, the concentration of the silver salt is higher in the latter impregnation solutions than in the first. In other instances, approximately equal amounts of silver are deposited during each impregnation. Often, to effect equal deposition in each impregnation, the silver concentration in the subsequent impregnation solutions may need to be greater than that in the initial impregnation solutions. In further instances, a greater amount of silver is deposited on the carrier in the initial impregnation than that deposited in subsequent impregnations. Each of the impregnations may be followed by roasting or other procedures to render the silver insoluble.

The catalyst prepared on the zircon-modified carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243, herein incorporated by reference. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst is not narrow and may vary over a wide range. The optimum alkali metal promoter concentration for a particular catalyst will be dependent upon performance characteristics, such as catalyst efficiency, rate of catalyst aging and reaction temperature.

The concentration of alkali metal (based on the weight of cation, for example cesium) in the finished catalyst may vary from about 0.0005 to 1.0 wt. %, preferably from about 0.005 to 0.5 wt. %. The preferred amount of cation promoter deposited on or present on the surface of the carrier or catalyst generally lies between about 10 and about 4000, preferably about 15 and about 3000, and more preferably between about 20 and about 2500 ppm by weight of cation calculated on the total carrier material. Amounts between about 50 and about 2000 ppm are frequently most preferable. When the alkali metal cesium is used in mixture with other cations, the ratio of cesium to any other alkali metal and alkaline earth metal salt(s), if used, to achieve desired performance is not narrow and may vary over a wide range. The ratio of cesium to the other cation promoters may vary from about 0.0001:1 to 10,000:1, preferably from about 0.001:1 to 1,000:1. Preferably, cesium comprises at least about 10, more preferably, about 20 to 100, percent (weight) of the total added alkali metal and alkaline earth metal in finished catalysts using cesium as a promoter.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $SO_4^{-2}$, phosphates, for example, $PO_4^{-3}$, titanates, e.g., $TiO_3^{-2}$, tantalates, for example, $Ta_2O_6^{-2}$, molybdates, for example, $MoO_4^{-2}$, vanadates, for example, $V_2O_4^{-2}$, chromates, for example, $CrO_4^{-2}$, zirconates, for example, $ZrO_3^{-2}$, polyphosphates, manganates, nitrates, chlorates, bromates, borates, silicates, carbonates, tungstates, thiosulfates, cerates and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

When the promoter comprises rhenium, the rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylenediaminetetraacetic acid (EDTA) or a suitable salt thereof.

The amount of anion promoter may vary widely, for example, from about 0.0005 to 2 wt. %, preferably from about 0.001 to 0.5 wt. % based on the total weight of the catalyst. When used, the rhenium component is often provided in an amount of at least about 1, say, at least about 5, for example, about 10 to 2000, often between 20 and 1000, ppmw calculated as the weight of rhenium based on the total weight of the catalyst.

The promoters for catalyst employing the present invention may also be of the type comprising at least one efficiency-enhancing salt of a member of a redox-half reaction pair which is employed in an epoxidation process in the presence of a gaseous nitrogen-containing component capable of forming a gaseous efficiency-enhancing member of a redox-half reaction pair under reaction conditions. The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213-1218 (1961) or "CRC Handbook of Chemistry and Physics", 65th Edition, CRC Press, Inc., Boca Raton, Fla., pages D155-162 (1984). The term "redox-half reaction pair" refers to the pairs of atoms, molecules or ions or mixtures thereof which undergo oxidation or reduction in such half-reaction equations. Such terms as redox-half reaction pairs are used herein to include those members of the class of substance which provide the desired performance enhancement, rather than a mechanism of the chemistry occurring. Preferably, such compounds, when associated with the catalyst as salts of members of a half reaction pair, are salts in which the anions are oxyanions, preferably an oxyanion of a polyvalent atom; that is, the atom of the anion to which oxygen is bonded is capable of existing, when bonded to a dissimilar atom, in different valence states. As used herein, the term "salt" does not indicate that the anion and cation components of the salt be associated or bonded in the solid catalyst, but only that both components be present in some form in the catalyst under reaction conditions. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The salt of a member of a redox-half reaction pair is added to the catalyst in an amount sufficient to enhance the efficiency of the epoxidation reaction. The precise amount will vary depending upon such variables as the gaseous efficiency-enhancing member of a redox-half reaction used and concentration thereof, the concentration of other components in the gas phase, the amount of silver contained in the catalyst, the surface area of the support, the process conditions, for example space velocity and temperature, and morphology of support. Alternatively, a suitable precursor compound may also be added such that the desired amount of the salt of a member of a redox-half reaction pair is formed in the catalyst under epoxidation conditions, especially through reaction with one or more of the gas-phase reaction components. Generally, however, a suitable range of concentration of the added efficiency-enhancing salt, or precursor thereof, calculated as cation, is about 0.01 to about 5%, preferably about 0.02 to about 3%, by weight, based on the total weight of the catalyst. Most preferably the salt is added in an amount of about 0.03 to about 2 wt. %.

The preferred gaseous efficiency-enhancing members of redox-half reaction pairs are compounds containing an element capable of existing in more than two valence states, preferably nitrogen and another element which is, preferably, oxygen. The gaseous component capable of producing a member of a redox-half reaction pair under reaction conditions is a generally a nitrogen-containing gas, such as for example nitric oxide, nitrogen dioxide and/or dinitrogen tetroxide, hydrazine, hydroxylamine or ammonia, nitroparaffins (for example, nitromethane), nitroaromatic compounds (for example nitrobenzene), N-nitro compounds, and nitriles (for example, acetonitrile). The amount of nitrogen-containing gaseous promoter to be used in these catalysts is that amount sufficient to enhance the performance, such as the activity of the catalyst and particularly the efficiency of the catalyst. The concentration of the nitrogen-containing gaseous promoter is determined by the particular efficiency-enhancing salt of a member of a redox-half reaction pair used and the concentration thereof, the particular alkene undergoing oxidation, and by other factors including the amount of carbon dioxide in the inlet reaction gases. For example, U.S. Pat. No. 5,504,053 discloses that when the nitrogen-containing gaseous promoter is NO (nitric oxide), a suitable concentration is from about 0.1 to about 100 ppm, by volume, of the gas stream.

Although in some cases it is preferred to employ members of the same half-reaction pair in the reaction system, that is, both the efficiency-enhancing salt promoter associated with the catalyst and the gaseous promoter member in the feedstream, as, for example, with a preferred combination of potassium nitrate and nitric oxide, this is not necessary in all cases to achieve satisfactory results. Other combinations, such as $KNO_2/N_2O_3$, $KNO_3/NO_2$, $KNO_3/N_2O_4$, $KNO_2/NO$, $KNO_2/NO_2$ may also be employed in the same system. In some instances, the salt and gaseous members may be found in different half-reactions which represent the first and last reactions in a series of half-reaction equations of an overall reaction.

In any event, the solid and/or gaseous promoters are provided in a promoting amount. As used herein the term "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Ethylene Epoxidation Process Conditions

A standard back-mixed autoclave with gas recycle is used for catalyst testing. There is some variation in gas phase feed concentrations depending on the process conditions used. Two cases are illustrated: air process conditions, which simulate typical conditions employed in commercial air-type ethylene epoxide processes where air is used to supply molecular oxygen, and oxygen process conditions, which simulate typical conditions in commercial oxygen-type ethylene oxide processes where pure oxygen is added as the oxygen source. Each case provides a different efficiency but it is the rule for practically all cases that with air as the oxygen feed, lower amounts of oxygen and ethylene are used which will yield an efficiency to ethylene epoxide which is about 2 to 5 percentage points lower than that when pure oxygen is employed as oxygen source. Well known, back-mixed, bottom-agitated "Magnedrive" autoclaves described in FIG. 2 of the paper by J. M. Berry entitled "Reactor for Vapor Phase-Catalytic Studies," in Chemical Engineering Progress, Vol. 70, No. 5, pages 78-84, 1974, are used as one of the reactors. The inlet conditions include the following:

TABLE I

Ethylene Epoxidation Inlet Process Conditions

| Component | Air Process Conditions-I Mole % | Oxygen Process Conditions-I Mole % | Oxygen Process Conditions-II Mole % |
|---|---|---|---|
| Ethylene | 11.0 | 30.0 | 30.0 |
| Oxygen | 7.0 | 8.0 | 8.0 |
| Ethane | 0.00-0.24 | 0.5 | 0.0 |
| Carbon Dioxide | 5.5 | 6.5 | 0.0 |
| Nitrogen | Balance of gas | Balance of gas | Balance of gas |
| Parts per million Ethyl Chloride | Optimum for Efficiency | Optimum for Efficiency | Optimum for Efficiency |
| Parts per million Nitric Oxide | None | None | Optimum for Efficiency |
| Type of Reactor | CSTR | CSTR | CSTR |
| Amount of Catalyst | 80 cc | 80 cc | 40 cc |
| Total Inlet Flow Rate | 22.6 SCFH | 22.6 SCFH | 11.3 SCFH |

The pressure is maintained at about 275 psig (pounds per square inch, gauge) and the total flow is maintained at about 11.3 or 22.6 SCFH (Standard Cubic Feet per Hour). SCFH refers to cubic feet per hour at standard temperature and pressure, namely, 0° C. and one atmosphere. Ethyl chloride concentration is adjusted to achieve maximum efficiency. Temperature (° C.) and catalyst efficiency are obtained as the responses describing the catalyst performance.

The catalyst test procedure used for autoclaves in the Ethylene Epoxidation Process Conditions involves the following: 40 or 80 cc of catalyst is charged to the back-mixed autoclave and the weight of the catalyst is noted. The back-mixed autoclave is heated to about reaction temperature in a nitrogen flow of 10 or 20 SCFH with the fan operating at 1500 rpm. The nitrogen flow is then discontinued and the above-described feed stream is introduced into the reactor. The total gas inlet flow is then adjusted to 11.3 SCFH for 40 cc of catalyst or 22.6 SCFH for 80 cc of catalyst. The temperature is adjusted over the next few hours to provide the desired percent outlet ethylene oxide and the optimum efficiency is obtained by adjusting ethyl chloride. The outlet epoxide concentration is monitored to make certain that the catalyst has reached its peak steady state performance. The ethyl chloride is periodically adjusted, and the efficiency of the catalyst to ethylene oxide and the rate of deactivation (temperature rise) is thus obtained. In determining activity and efficiency, the process and catalyst should be under steady state conditions.

The standard deviation of a single test result reporting catalyst efficiency in accordance with the procedure described above is about 0.3% efficiency units. The typical standard deviation of a single test result reporting catalyst activity in accordance with the procedure described above is about 1.2° C. The standard deviation, of course, will depend upon the quality of the equipment and precision of the techniques used in conducting the tests, and thus will vary. These standard deviations are believed to apply to the test results reported herein.

The properties of the starting carrier materials and the specifics of their modifications are detailed in Table II. Table III sets forth the specifics of the catalyst preparations on the carriers of Table II, including catalyst compositions.

Carrier Preparations

Carriers of the examples were prepared in the following manner. Zirconium silicate (if used) was added with other solid raw materials to obtain a dry mixture. In all cases where zircon was used, it was introduced in a powder form with a median particle size of about 130 microns. Liquids and additional dry raw materials (optional) were then added. The amounts of such additives are expressed as percentages by weight of the starting dry mixture. Water was also added in an amount sufficient to obtain an extrudable mixture. Such amount depends on a number of factors, such as ambient humidity, hydration level of the raw materials, etc. Unless otherwise noted in the following descriptions, the mixture was extruded as cylinders with a single opening along the axis, or as multi-partitioned cylinders. After drying, the extruded greenware was fired to alpha-alumina under conditions chosen to ensure complete conversion of the extrudates to alpha-alumina. Firing temperatures between 1000° C. and 1400° C. and firing times from 45 minutes to 5 hours were used. Outer diameter dimensions of the fired greenware were 0.31-0.35 inches, cylinder lengths 0.29-0.34 inches, and the wall thickness of the multi-partitioned cylinders no greater than 0.075 inches. Physical properties and the approximate weight percent of zircon in the modified carriers and comparative carriers are given in Table II. All percentages in the following descriptions are in weight percent.

TABLE II

| Carrier Properties | | | | | | | | | | | | | |
|---|---|---|---|---|---|---|---|---|---|---|---|---|---|
| Carrier ID | A | B | C | D | E | F | G | H | I | J | K | L | M |
| Surface Area (m$^2$/g) | 1.04 | 1.18 | 1.29 | 1.01 | 1.46 | 1.19 | 0.49 | 0.63 | 0.94 | 0.60 | 0.52 | 0.49 | 0.54 |
| Packing Density (lb/ft$^3$) | 32.5 | 33.1 | 34.2 | 34.6 | 25.5 | 24.9 | 27.4 | 25.5 | 25.4 | 31.4 | 32.5 | 30.4 | 30.5 |

TABLE II-continued

Carrier Properties

| Carrier ID | A | B | C | D | E | F | G | H | I | J | K | L | M |
|---|---|---|---|---|---|---|---|---|---|---|---|---|---|
| Pore Volume (cc/g) | 0.68 | 0.63 | 0.61 | 0.66 | 0.76 | 0.80 | 0.59 | 0.77 | 0.92 | 0.53 | 0.56 | 0.63 | 0.65 |
| Zircon Target (Wt. %) | 2 | 0 | 1 | 0 | 2 | 0 | 3 | 0.3 | 0 | 2 | 0 | 2 | 0 |

Carrier A was prepared from calcined alumina which originally contained 0.06 wt. % CaO. The alumina was combined with a 10% acetic acid solution and heated at 100° C. for 15 minutes with stirring, then filtered and vacuum rinsed twice with hot deionized water. The leached alumina was dried overnight at 100° C. and was found to contain 0.03% CaO. A dry mixture was prepared from 71.1% of the leached alumina, 22.8% organic pore-forming burnout, 4.5% extrusion aids, <1% flux material and 1.4% granular zircon. 2.1 Percent additional extrusion aid and <1% surfactant were added as aqueous slurries with sufficient water to form an extrudable blend. This blend was extruded, dried and fired to alpha alumina. The final sample contained about 2% zircon.

Comparative Carrier B was prepared in a similar manner as Carrier A except that no zircon was added.

Carrier C was prepared by blending a dry mixture of 79.2% pseudoboehmite, 19.8% gamma-alumina and 1% granular zircon. 5.5% formic acid and 4.6% ammonium bifluoride were added as aqueous solutions with sufficient water to form an extrudable blend. After mixing, the blend was extruded, dried and fired to alpha-alumina. The final sample contained about 1% zircon.

Comparative Carrier D was prepared using the same procedure as that given above for Carrier C except that no zircon was added.

Carrier E was prepared by blending a dry mixture of 75.5% gibbsite, 22.5% pseudoboehmite, and 2.0% granular zircon. To this dry mixture was added 31.4% graphite with a particle size less than 600 microns. 1.7% Ammonium fluoride, 2.0% magnesium nitrate hydrate and 1.2% nitric acid were then added as aqueous solutions with an appropriate amount of water to form an extrudable blend. After mixing, the blend was extruded, dried and fired to alpha-alumina. The final sample contained about 2% zircon.

Comparative Carrier F was prepared using the same procedure as that given above for Carrier E except that no zircon was added.

Carrier G was prepared by blending a dry mixture of 74.8% gibbsite, 22.3% pseudoboehmite and 2.9% granular zircon. To this dry mixture was added 21.4% graphite with a particle size less than 600 microns. 4.6% Nitric acid, 1.9% magnesium nitrate hydrate and 1.6% ammonium fluoride were then added as aqueous solutions with an appropriate amount of water to form an extrudable blend. This blend was extruded, dried and fired to alpha alumina. The final sample contained about 3% zircon.

Carrier H was prepared in an analogous manner to Carrier G except that the amount of granular zircon added was sufficient to give about 0.3% zircon by weight in the finished carrier.

Carrier I was prepared in an analogous manner to Carrier G except that no zircon was added.

Carrier J was prepared by blending a dry mixture of 68.6% pseudoboehmite, 29.4% gibbsite and 2.0% zircon. To this mixture was added <1% hydroxypropyl methylcellulose. 5.4% Acetic acid and 4.0% hydrofluoric acid were then added as aqueous solutions with an appropriate amount of water to form an extrudable blend. The mixture was extruded, dried and fired to alpha-alumina. The final sample contained about 2% zircon.

Comparative Carrier K was prepared in an analogous manner to Carrier J except that no zircon was added.

Carrier L was prepared by blending a mixture of 98% pseudoboehmite with 2% granular zircon, 5.4% formic acid and 2.1% hydrofluoric acid were then added as aqueous solutions with an appropriate amount of water to form an extrudable blend. The mixture was extruded, dried and fired to alpha-alumina. The final sample contained about 2% zircon.

Comparative Carrier M was prepared in an analogous manner to Carrier except that no zircon was added.

Catalyst Preparations

The carriers were vacuum impregnated with a first impregnation silver solution typically containing 30 wt. % silver oxide, 18 wt. % oxalic acid, 17 weight percent ethylenediamine, 6 wt. % monoethanolamine, and 27 wt. % distilled water. The first impregnation solution was typically prepared by (1) mixing 1.14 parts of ethylenediamine (high purity grade) with 1.75 parts of distilled water; (2) slowly adding 1.16 parts of oxalic acid dihydrate (reagent grade) to the aqueous ethylenediamine solution such that the temperature of the solution does not exceed 40° C., (3) slowly adding 1.98 parts of silver oxide, and (4) adding 0.40 parts of monoethanolamine (Fe and Cl free).

The carrier was impregnated in an appropriately sized glass or stainless steel cylindrical vessel which was equipped with suitable stopcocks for impregnating the carrier under vacuum. A suitable separatory funnel which was used for containing the impregnating solution was inserted through a rubber stopper into the top of the impregnating vessel. The impregnating vessel containing the carrier was evacuated to approximately 1-2"mercury absolute for 10 to 30 minutes, after which the impregnating solution was slowly added to the carrier by opening the stopcock between the separatory funnel and the impregnating vessel. After all the solution emptied into the impregnating vessel (~15 seconds), the vacuum was released and the pressure returned to atmospheric. Following addition of the solution, the carrier remained immersed in the impregnating solution at ambient conditions for 5 to 30 minutes, and was thereafter drained of excess solution for 10 to 30 minutes.

The silver-impregnated carrier was then roasted as follows to effect reduction of silver on the catalyst surface. The impregnated carrier was spread out in a single layer on stainless steel wire mesh trays then placed on a stainless steel belt (spiral weave) and transported through a 2"×2" square heating zone for 2.5 minutes, or equivalent conditions were used for a larger belt operation. The heating zone was maintained at 500° C. by passing hot air upward through the belt and about the catalyst particles at the rate of 266 standard cubic feet per hour (SCFH). After being roasted in the heating zone, the catalyst was cooled in the open air to room temperature and weighed.

Next, the silver-impregnated carrier was vacuum impregnated with a second silver impregnation solution containing both the silver oxalate amine solution and the catalyst promoters. The second impregnation solution was composed of all of the drained solution from the first impregnation plus a fresh aliquot of the first solution, or a new solution was used. The promoters, in either aqueous solution or neat form, were added (in the ascending numeric order listed in Table III) with stirring. In Catalysts 3 through 10, two equivalents of diammonium ethylenediaminetetraacetic acid (EDTA) were added with the manganese promoter in order to stabilize the manganese in the impregnation solution. In Catalysts 11 and 12, one excess equivalent of diammonium EDTA was added for the same purpose.

The impregnation, draining and roasting steps for this second impregnation were carried out analogously to the first impregnation.

The twice-impregnated carrier, that is, the finished catalyst, was again weighed, and based upon the weight gain of the carrier in the second impregnation, the weight percent of silver and the concentration of the promoters were calculated (results given in Table III). In some cases, the preparation of a catalyst was carried out on a larger scale than that described here using suitable scale-up of equipment and methods. The finished catalyst was then employed in an ethylene epoxidation reaction, the results of which are given in the Examples.

TABLE III

Catalyst Preparations

| | Catalyst No. | | | |
|---|---|---|---|---|
| | 1 | 2 | 3 | 4 |
| Carrier No. | A | B | C | D |
| Promoter 1 | $Na_2SO_4$ | $Na_2SO_4$ | CsOH | CsOH |
| Promoter 2 | $Cs_2SO_4$ | $Cs_2SO_4$ | $Cs_2SO_4$ | $Cs_2SO_4$ |
| Promoter 3 | | | $Mn(NO_3)_2$ | $Mn(NO_3)_2$ |
| Chelating Agent | | | $(NH_4)_2H_2(EDTA)$ | $(NH_4)_2H_2(EDTA)$ |
| Total Wt. % Silver | 30.95 | 30.7 | 35.40 | 32.88 |
| Promoter 1; ppm | 340 Na | 385 Na | 575 Cs | 552 Cs |
| Promoter 2; ppm | 653 Cs | 742 Cs | 162 SO4 | 150 SO4 |
| Promoter 3; ppm | | | 104 Mn | 94 Mn |

| | Catalyst No. | | | |
|---|---|---|---|---|
| | 5 | 6 | 7 | 8 |
| Carrier No. | E | F | G | H |
| Promoter 1 | CsOH | CsOH | CsOH | CsOH |
| Promoter 2 | $Cs_2SO_4$ | $Cs_2SO_4$ | $Cs_2SO_4$ | $Cs_2SO_4$ |
| Promoter 3 | $Cs_2MoO_4$ | $Cs_2MoO_4$ | $Mn(NO_3)_2$ | $Mn(NO_3)_2$ |
| Promoter 4 | $Mn(NO_3)_2$ | $Mn(NO_3)_2$ | | |
| Chelating Agent | $(NH_4)_2H_2(EDTA)$ | $(NH_4)_2H_2(EDTA)$ | $(NH_4)_2H_2(EDTA)$ | $(NH_4)_2H_2(EDTA)$ |
| Total Wt. % Silver | 34.8 | 35.6 | 37.0 | 38.8 |
| Promoter 1; ppm | 584 Cs | 796 Cs | 409 Cs | 420 Cs |
| Promoter 2; ppm | 129 SO4 | 175 SO4 | 115 SO4 | 118 SO4 |
| Promoter 3; ppm | 15 Mo | 20 Mo | 74 Mn | 77 Mn |
| Promoter 4; ppm | 53 Mn | 71 Mn | | |

| | Catalyst No. | | | |
|---|---|---|---|---|
| | 9 | 10 | 11 | 12 |
| Carrier No. | I | J | K | L |
| Promoter 1 | CsOH | CsOH | CsOH | CsOH |
| Promoter 2 | $Cs_2SO_4$ | $Cs_2SO_4$ | $Cs_2SO_4$ | $Cs_2SO_4$ |
| Promoter 3 | $Mn(NO_3)_2$ | $Mn(NO_3)_2$ | $Mn(NO_3)_2$ | $Cs_2MoO_4$ |
| Promoter 4 | | | | $Mn(NO_3)_2$ |
| Chelating Agent | $(NH_4)_2H_2(EDTA)$ | $(NH_4)_2H_2(EDTA)$ | $(NH_4)_2H_2(EDTA)$ | $(NH_4)_2H_2(EDTA)$ |
| Total Wt. % Silver | 39.5 | 28.4 | 27.4 | 32.2 |
| Promoter 1; ppm | 489 Cs | 439 Cs | 383 Cs | 364 Cs |
| Promoter 2; ppm | 138 SO4 | 123 SO4 | 108 SO4 | 81 SO4 |
| Promoter 3; ppm | 89 Mn | 79 Mn | 70 Mn | 9 Mo |
| Promoter 4; ppm | | | | 32 Mn |

| | Catalyst No. | | |
|---|---|---|---|
| | 13 | 14 | 15 |
| Carrier No. | M | J | K |
| Promoter 1 | CsOH | $KNO_3$ | $KNO_3$ |
| Promoter 2 | $Cs_2SO_4$ | $K_2Mn(EDTA)$ | $K_2Mn(EDTA)$ |
| Promoter 3 | $Cs_2MoO_4$ | | |
| Promoter 4 | $Mn(NO_3)_2$ | | |

TABLE III-continued

| Catalyst Preparations | | | |
|---|---|---|---|
| Chelating Agent | $(NH_4)_2H_2(EDTA)$ | $(NH_4)_2H_2(EDTA)$ | $(NH_4)_2H_2(EDTA)$ |
| Total Wt. % Silver | 32.9 | 31.5 | 32.7 |
| Promoter 1; ppm | 373 Cs | 957 K | 965 K |
| Promoter 2; ppm | 83 SO4 | 144 Mn | 144 Mn |
| Promoter 3; ppm | 9 Mo | | |
| Promoter 4; ppm | 33 Mn | | |

In Tables IV through X "Mlb EO/CF" denotes units of 1000 pounds of ethylene oxide produced per cubic foot of catalyst.

EXAMPLE 1

Catalyst 1 and Comparative Catalyst 2

Eighty cubic centimeters of each catalyst (61.4 g.) was charged to an autoclave reactor and tested under Air Process Conditions-I (Table I). Outlet ethylene oxide was set to 1.2 mole percent until day 6 when it was increased to 1.4 mole percent. Table IV compares the performance of the catalyst containing 2 weight percent zircon (Catalyst 1) with one containing no zircon (Comparative Catalyst 2). The catalyst containing zircon has higher initial efficiency and lower initial temperature (higher activity).

TABLE IV

| Example 1 Catalyst Performance | | | | | | |
|---|---|---|---|---|---|---|
| | Efficiency % | | | Temp. ° C. | | |
| | 2 Mlb EO/CF | 5 Mlb EO/CF | 7 Mlb EO/CF | 2 Mlb EO/CF | 5 Mlb EO/CF | 7 Mlb EO/CF |
| Catalyst 1 | 76.4 | 74.7 | 71.7 | 260 | 269 | 280 |
| Catalyst 2 (comparative) | 74.8 | 73.4 | 71.6 | 266 | 274 | 281 |

EXAMPLE 2

Catalyst 3 and Comparative Catalyst 4

An equal weight (63.5 g.) of each catalyst was charged to an autoclave reactor and tested under the Air Process Conditions-I described in Table I. The outlet ethylene oxide was set to 1.4 mole percent and temperature and efficiency monitored as the catalysts aged. Table V compares performance of the two catalysts as a function of pounds of EO produced per cubic foot of catalyst. Although the initial efficiency is lower than the comparative catalyst, over time, the zircon-containing catalyst ages in efficiency and temperature at a slower rate.

TABLE V

| Example 2 Catalyst Performance | | | | | | |
|---|---|---|---|---|---|---|
| | Efficiency % | | | Temp. ° C. | | |
| | 8 Mlb EO/CF | 20 Mlb EO/CF | 35 Mlb EO/CF | 8 Mlb EO/CF | 20 Mlb EO/CF | 35 Mlb EO/CF |
| Catalyst 3 | 78.2 | 77.7 | 77.2 | 249 | 253 | 256 |
| Catalyst 4 (comparative) | 79.9 | 78.4 | 75.9 | 243 | 251 | 259 |

EXAMPLE 3

Catalyst 5 and Comparative Catalyst 6

An equal weight (63.5 g.) of each catalyst was tested in an autoclave under Oxygen Process Conditions-I (Table I). Outlet ethylene oxide concentration was set to 1.0 mole percent. Catalyst 5 has higher efficiency and lower temperature compared to Comparative Catalyst 6, which does not contain zircon.

TABLE VI

| Example 3 Catalyst Performance | | | | |
|---|---|---|---|---|
| | Efficiency (%) | | Temp. (° C.) | |
| | 1 Mlb EO/CF | 2.5 Mlb EO/CF | 1 Mlb EO/CF | 2.5 Mlb EO/CF |
| Catalyst 5 | 80.4 | 80.0 | 232 | 230 |
| Catalyst 6 (comparative) | 76.6 | 77.7 | 253 | 253 |

EXAMPLE 4

Catalyst 7, Catalyst 8 and Comparative Catalyst 9

An equal weight (63.5 g.) of each catalyst was tested in an autoclave under Oxygen Process Conditions-I (Table I). Outlet ethylene oxide concentration was set to 1.2 mole percent. Catalyst 8, which contains ~0.3% zircon has the highest efficiency and lowest efficiency aging and temperature aging. Catalyst 7, which contains ~3% zircon is more active and efficient than Comparative Catalyst 9 which contains no added zircon.

TABLE VII

| Example 4 Catalyst Performance | | | | | | |
|---|---|---|---|---|---|---|
| | Efficiency % | | | Temp. ° C. | | |
| | 1.5 Mlb EO/CF | 5.0 Mlb EO/CF | 7.0 Mlb EO/CF | 1.5 Mlb EO/CF | 5.0 Mlb EO/CF | 7.0 Mlb EO/CF |
| Catalyst 7 | 79.8 | 78.2 | 76.0 | 244 | 250 | 256 |
| Catalyst 8 | 80.2 | 79.6 | 78.3 | 246 | 244 | 246 |
| Catalyst 9 (comparative) | 79.5 | 76.0 | — | 251 | 262 | — |

EXAMPLE 5

Catalyst 10 and Comparative Catalyst 11

An equal weight (63.5 g.) of each catalyst was tested in an autoclave under Oxygen Process Conditions-I. Outlet ethylene oxide concentration was set to 1.0 mole percent. Catalyst 10 shows more stable temperature than Comparative Catalyst 11 which does not contain zircon.

TABLE VIII

Example 5 Catalyst Performance

|  | Efficiency % | | | Temp. ° C. | | |
| --- | --- | --- | --- | --- | --- | --- |
|  | 1 Mlb EO/CF | 3 Mlb EO/CF | 5 Mlb EO/CF | 1 Mlb EO/CF | 3 Mlb EO/CF | 5 Mlb EO/CF |
| Catalyst 10 | 80.9 | 81.1 | 80.1 | 231 | 230 | 230 |
| Catalyst 11 (comparative) | 80.8 | 81.1 | 80.0 | 233 | 233 | 235 |

EXAMPLE 6

Catalyst 12 and Comparative Catalyst 13

An equal weight (63.5 g.) of each catalyst was tested in an autoclave under Oxygen Process Conditions-I. Outlet ethylene oxide concentration was set to 1.0 mole percent. Catalyst 12, prepared with zircon, is initially less efficient and less active, but shows significantly lower temperature aging than Comparative Catalyst 13, prepared without zircon.

TABLE IX

Example 6 Catalyst Performance

|  | Efficiency % | | | Temp. ° C. | | |
| --- | --- | --- | --- | --- | --- | --- |
|  | 2 Mlb EO/CF | 5 Mlb EO/CF | 7.5 Mlb EO/CF | 2 Mlb EO/CF | 5 Mlb EO/CF | 7.5 Mlb EO/CF |
| Catalyst 12 | 80.7 | 79.8 | 79.2 | 242 | 242 | 244 |
| Catalyst 13 (comparative) | 81.1 | 80.5 | 79.6 | 241 | 244 | 248 |

EXAMPLE 7

Catalyst 14 and Comparative Catalyst 15

Thirty cubic centimeters (26.8 g. for Comparative Catalyst 14 and 26.1 g. for Catalyst 15) of each catalyst was charged to an autoclave reactor and tested under Oxygen Process Conditions-II (Table I). After initial operation at temperatures between 220 and 255° C., conditions were adjusted for a total flow of 21.3 SCFH, and temperature was controlled to maintain 1.2 mole percent outlet ethylene oxide. Initial efficiency of Catalyst 14, which contains zircon is higher than that of Comparative Catalyst 15, and the efficiency decline rate is reduced.

TABLE X

Example 7 Catalyst Performance

|  | Efficiency % | | | Temp. ° C. | | |
| --- | --- | --- | --- | --- | --- | --- |
|  | Day 12 | Day 16 | Day 21 | Day 12 | Day 16 | Day 21 |
| Catalyst 14 | 86.3 | 86.5 | 86.1 | 246 | 247 | 248 |
| Catalyst 15 (comparative) | 84.5 | 84.3 | 83.4 | 247 | 248 | 250 |

What is claimed is:

1. A catalyst for the manufacture of alkylene oxide by the vapor-phase epoxidation of alkene, said catalyst comprising impregnated silver and at least one efficiency-enhancing promoter on a refractory solid support, wherein the refractory solid support comprises zirconium silicate in an amount from about 0.3 to 3.0% by weight of zirconium silicate based on the total weight of the support wherein the refractory solid support, exclusive of zirconium silicate, is at least 95% by weight alpha alumina, and wherein the refractory solid support, exclusive of zirconium silicate, contains less than about 500 ppmw alkaline earth metal excluding calcium compounds, measured as the alkaline earth metal oxide, and less than about 350 ppmw calcium.

2. The catalyst of claim 1 wherein the impregnated silver is present from about 2 to 60% by weight of the catalyst.

3. The catalyst of claim 2 wherein the impregnated silver is present from about 5 to 50% by weight of the catalyst.

4. The catalyst of claim 3 wherein the impregnated silver is present from about 10 to 40% by weight of the catalyst.

5. The catalyst of claim 1 wherein at least one of the efficiency enhancing promoters comprises at least one alkali metal, alkaline earth metal and/or oxyanion of an element, other than oxygen, having an atomic number of 5 to 83 and being selected from groups 3b through 7b and 3a through 7a of the Periodic Table.

6. The catalyst of claim 1 wherein at least one of the efficiency-enhancing promoters is an efficiency enhancing salt of a member of a redox-half reaction pair.

7. The catalyst of claim 1 wherein at least one of the efficiency-enhancing promoters is a rhenium component.

8. The catalyst of claim 1 wherein the refractory solid support, exclusive of zirconium silicate, is at least 99% by weight alpha alumina.

9. The catalyst of claim 8 wherein the refractory solid support has a morphology comprising interlocking platelets of alpha-alumina.

10. The catalyst of claim 1 wherein the refractory solid support has a surface area of at least about 0.5 m2/g, a pore volume of at least about 0.5 cc/g, and a median pore diameter between about 1 to 50 microns.

* * * * *